US010612017B2

United States Patent
Hinz et al.

(10) Patent No.: US 10,612,017 B2
(45) Date of Patent: Apr. 7, 2020

(54) SCAFFOLDED NUCLEIC ACID POLYMER PARTICLES AND METHODS OF MAKING AND USING

(71) Applicant: LIFE TECHNOLOGIES CORPORATION, Carlsbad, CA (US)

(72) Inventors: Wolfgang Hinz, Carlsbad, CA (US); John Leamon, Stonington, CT (US); David Light, Branford, CT (US); Jonathan M. Rothberg, Guilford, CT (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 16/121,615

(22) Filed: Sep. 4, 2018

(65) Prior Publication Data

US 2019/0071667 A1 Mar. 7, 2019

Related U.S. Application Data

(60) Continuation of application No. 15/846,195, filed on Dec. 18, 2017, now abandoned, which is a division of
(Continued)

(51) Int. Cl.
*C12Q 1/68* (2018.01)
*C12N 15/10* (2006.01)
(Continued)

(52) U.S. Cl.
CPC ...... *C12N 15/1093* (2013.01); *B01J 19/0046* (2013.01); *C12Q 1/6874* (2013.01);
(Continued)

(58) Field of Classification Search
None
See application file for complete search history.

(56) References Cited

U.S. PATENT DOCUMENTS

| 4,722,830 A | 2/1988 | Urie et al. |
| 4,822,566 A | 4/1989 | Newman |

(Continued)

FOREIGN PATENT DOCUMENTS

| CN | 101413034 | 2/2011 |
| WO | WO-2005084367 | 9/2005 |

(Continued)

OTHER PUBLICATIONS

Rehman et al, Nuc. Acids Res., vol. 27, pp. 649-655 (1999).*
(Continued)

*Primary Examiner* — Robert T. Crow

(57) ABSTRACT

The invention provides particle compositions having applications in nucleic acid analysis. Nucleic acid polymer particles of the invention allow polynucleotides to be attached throughout their volumes for higher loading capacities than those achievable solely with surface attachment. In one aspect, nucleic acid polymer particles of the invention comprise polyacrylamide particles with uniform size distributions having low coefficients of variations, which result in reduced particle-to-particle variation in analytical assays. Such particle compositions are used in various amplification reactions to make amplicon libraries from nucleic acid fragment libraries.

20 Claims, 8 Drawing Sheets

Related U.S. Application Data application No. 14/987,552, filed on Jan. 4, 2016, now abandoned, which is a continuation of application No. 14/044,712, filed on Oct. 2, 2013, now Pat. No. 9,249,461, which is a continuation of application No. 12/785,685, filed on May 24, 2010, now Pat. No. 8,574,835, which is a continuation-in-part of application No. 12/475,311, filed on May 29, 2009, now abandoned, which is a continuation-in-part of application No. 12/474,897, filed on May 29, 2009, now abandoned.

(60) Provisional application No. 61/297,203, filed on Jan. 21, 2010, provisional application No. 61/291,788, filed on Dec. 31, 2009, provisional application No. 61/263,734, filed on Nov. 23, 2009, provisional application No. 61/242,369, filed on Sep. 14, 2009.

(51) Int. Cl.
  *B01J 19/00* (2006.01)
  *C40B 40/08* (2006.01)
  *C40B 50/06* (2006.01)
  *C12Q 1/6874* (2018.01)

(52) U.S. Cl.
  CPC .............. *C40B 40/08* (2013.01); *C40B 50/06* (2013.01); *B01J 2219/005* (2013.01); *B01J 2219/00466* (2013.01); *B01J 2219/00596* (2013.01); *B01J 2219/00722* (2013.01); *Y10T 428/2982* (2015.01)

(56) References Cited

U.S. PATENT DOCUMENTS

| | | |
|---|---|---|
| 4,863,849 A | 9/1989 | Melamede |
| 4,874,499 A | 10/1989 | Smith et al. |
| 4,971,903 A | 11/1990 | Hyman |
| 5,038,192 A | 8/1991 | Bonneau et al. |
| 5,057,426 A | 10/1991 | Henco et al. |
| 5,110,441 A | 5/1992 | Kinklen et al. |
| 5,284,566 A | 2/1994 | Cuomo et al. |
| 5,317,407 A | 5/1994 | Michon |
| 5,466,348 A | 11/1995 | Holm-Kennedy |
| 5,478,893 A | 12/1995 | Ghosh et al. |
| 5,554,339 A | 9/1996 | Cozzette et al. |
| 5,593,838 A | 1/1997 | Zanzucchi et al. |
| 5,702,964 A | 12/1997 | Lee |
| 5,846,708 A | 12/1998 | Hollis et al. |
| 5,854,033 A | 12/1998 | Lizardi |
| 5,922,591 A | 7/1999 | Anderson et al. |
| 5,932,450 A | 8/1999 | Dattagupta et al. |
| 5,965,452 A | 10/1999 | Kovacs |
| 6,090,935 A | 7/2000 | Breivik et al. |
| 6,255,678 B1 | 7/2001 | Sawada et al. |
| 6,274,320 B1 | 8/2001 | Rothberg et al. |
| 6,327,410 B1 | 12/2001 | Walt et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,465,178 B2 | 10/2002 | Chappa et al. |
| 6,482,639 B2 | 11/2002 | Snow et al. |
| 6,499,499 B2 | 12/2002 | Dantsker et al. |
| 6,511,803 B1 | 1/2003 | Church et al. |
| 6,613,513 B1 | 9/2003 | Parce et al. |
| 6,642,000 B1 | 11/2003 | Strizhkov et al. |
| 6,682,899 B2 | 1/2004 | Bryan et al. |
| 6,700,814 B1 | 3/2004 | Nahas et al. |
| 6,780,591 B2 | 8/2004 | Williams et al. |
| 6,806,052 B2 | 10/2004 | Bridgham et al. |
| 6,828,100 B1 | 12/2004 | Ronaghi |
| 6,859,570 B2 | 2/2005 | Walt et al. |
| 6,953,958 B2 | 10/2005 | Baxter et al. |
| 6,969,488 B2 | 11/2005 | Bridgham et al. |
| 6,998,274 B2 | 2/2006 | Chee et al. |
| 7,033,754 B2 | 4/2006 | Chee et al. |
| 7,037,687 B2 | 5/2006 | Ashton |
| 7,049,645 B2 | 5/2006 | Sawadai et al. |
| 7,060,431 B2 | 6/2006 | Chee et al. |
| 7,087,387 B2 | 8/2006 | Gerdes et al. |
| 7,090,975 B2 | 8/2006 | Shultz et al. |
| 7,097,973 B1 | 8/2006 | Zenhausern |
| 7,105,300 B2 | 9/2006 | Parce et al. |
| 7,192,700 B2 | 3/2007 | Mckeown |
| 7,211,390 B2 | 5/2007 | Rothberg et al. |
| 7,223,540 B2 | 5/2007 | Pourmand et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,264,934 B2 | 9/2007 | Fuller |
| 7,276,749 B2 | 10/2007 | Martin et al. |
| 7,291,496 B2 | 11/2007 | Holm-Kennedy |
| 7,303,875 B1 | 12/2007 | Bock et al. |
| 7,317,216 B2 | 1/2008 | Holm-Kennedy |
| 7,323,305 B2 | 1/2008 | Leamon et al. |
| 7,335,762 B2 | 2/2008 | Rothberg et al. |
| 7,595,883 B1 | 9/2009 | El Gamal et al. |
| 7,815,868 B1 | 10/2010 | Jones et al. |
| 7,888,015 B2 | 2/2011 | Toumazou et al. |
| 7,948,015 B2 | 5/2011 | Rothberg et al. |
| 8,574,835 B2 | 11/2013 | Hinz et al. |
| 9,249,461 B2 | 2/2016 | Hinz et al. |
| 2002/0042059 A1 | 4/2002 | Makarov et al. |
| 2002/0094533 A1 | 7/2002 | Hess et al. |
| 2002/0117694 A1 | 8/2002 | Migliorato et al. |
| 2002/0131899 A1 | 9/2002 | Kovacs et al. |
| 2003/0036064 A1 | 2/2003 | Stuelpnagel et al. |
| 2003/0068629 A1 | 4/2003 | Rothberg et al. |
| 2003/0073086 A1* | 4/2003 | Guire .................. B01J 19/0046 506/9 |
| 2003/0108867 A1 | 6/2003 | Chee et al. |
| 2003/0124599 A1 | 7/2003 | Chen et al. |
| 2003/0162891 A1 | 8/2003 | Panattoni |
| 2003/0186262 A1 | 10/2003 | Cailloux |
| 2003/0211637 A1 | 11/2003 | Schoeniger et al. |
| 2004/0023253 A1 | 2/2004 | Kunwar et al. |
| 2004/0134798 A1 | 7/2004 | Toumazou et al. |
| 2004/0136866 A1 | 7/2004 | Pontis et al. |
| 2004/0185484 A1 | 9/2004 | Costa et al. |
| 2004/0197803 A1 | 10/2004 | Yaku et al. |
| 2004/0235216 A1 | 11/2004 | Rhodes |
| 2005/0006234 A1 | 1/2005 | Hassibi |
| 2005/0019842 A1 | 1/2005 | Prober et al. |
| 2005/0032076 A1 | 2/2005 | Williams et al. |
| 2005/0042627 A1 | 2/2005 | Chakrabarti et al. |
| 2005/0065224 A1 | 3/2005 | Menzler et al. |
| 2005/0079510 A1 | 4/2005 | Berka et al. |
| 2005/0130188 A1 | 6/2005 | Walt et al. |
| 2005/0136414 A1 | 6/2005 | Gunderson et al. |
| 2005/0212016 A1 | 9/2005 | Brunner et al. |
| 2005/0227264 A1 | 10/2005 | Nobile et al. |
| 2005/0230271 A1 | 10/2005 | Levon et al. |
| 2006/0024711 A1 | 2/2006 | Lapidus et al. |
| 2006/0040297 A1 | 2/2006 | Leamon et al. |
| 2006/0093488 A1 | 5/2006 | Wong et al. |
| 2006/0105373 A1 | 5/2006 | Pourmand et al. |
| 2006/0121670 A1 | 6/2006 | Stasiak |
| 2006/0197118 A1 | 9/2006 | Migliorato et al. |
| 2006/0199193 A1 | 9/2006 | Koo et al. |
| 2006/0219558 A1 | 10/2006 | Hafeman et al. |
| 2006/0228721 A1 | 10/2006 | Leamon et al. |
| 2006/0246497 A1 | 11/2006 | Huang et al. |
| 2007/0087362 A1 | 4/2007 | Church et al. |
| 2007/0087401 A1 | 4/2007 | Neilson et al. |
| 2007/0092872 A1 | 4/2007 | Rothberg et al. |
| 2007/0109454 A1 | 5/2007 | Chou |
| 2007/0117099 A1 | 5/2007 | Engelhardt et al. |
| 2007/0212681 A1 | 9/2007 | Shapiro et al. |
| 2007/0262363 A1 | 11/2007 | Tao et al. |
| 2008/0003142 A1 | 1/2008 | Link et al. |
| 2008/0102466 A1 | 5/2008 | Macevicz |
| 2008/0115361 A1 | 5/2008 | Santini et al. |
| 2008/0121946 A1 | 5/2008 | Youn et al. |

(56) References Cited

U.S. PATENT DOCUMENTS

| | | |
|---|---|---|
| 2008/0145910 A1 | 6/2008 | Ward et al. |
| 2008/0166727 A1 | 7/2008 | Esfandyarpour et al. |
| 2008/0230386 A1 | 9/2008 | Srinivasan et al. |
| 2008/0242560 A1 | 10/2008 | Gunderson et al. |
| 2008/0265985 A1 | 10/2008 | Toumazou et al. |
| 2008/0286767 A1 | 11/2008 | Miyahara et al. |
| 2009/0026082 A1 | 1/2009 | Rothberg et al. |
| 2009/0062132 A1 | 3/2009 | Borner |
| 2010/0137143 A1 | 6/2010 | Rothberg et al. |
| 2010/0188073 A1 | 7/2010 | Rothberg et al. |
| 2010/0282617 A1 | 11/2010 | Rothberg et al. |
| 2010/0301398 A1 | 12/2010 | Rothberg et al. |
| 2011/0195252 A1 | 8/2011 | Hinz et al. |
| 2011/0195253 A1 | 8/2011 | Hinz et al. |
| 2011/0201506 A1 | 8/2011 | Hinz et al. |
| 2011/0201508 A1 | 8/2011 | Hinz et al. |
| 2011/0201523 A1 | 8/2011 | Hinz et al. |
| 2011/0263463 A1 | 10/2011 | Rothberg et al. |
| 2011/0275522 A1 | 11/2011 | Rothberg et al. |
| 2012/0094871 A1 | 4/2012 | Hinz et al. |
| 2016/0194629 A1 | 7/2016 | Hinz et al. |
| 2018/0179520 A1 | 6/2018 | Hinz et al. |

FOREIGN PATENT DOCUMENTS

| | | |
|---|---|---|
| WO | WO-2007133710 | 11/2007 |
| WO | WO-2008107014 | 9/2008 |
| WO | WO-2008109176 | 9/2008 |
| WO | WO-2009158006 | 12/2009 |
| WO | WO-2010008480 | 1/2010 |
| WO | WO-2010047804 | 4/2010 |
| WO | WO-2010138186 | 12/2010 |
| WO | WO-2010138187 | 12/2010 |
| WO | WO-2010138188 | 12/2010 |

OTHER PUBLICATIONS

Akiyama et al., "Ion-Sensitive Field-Effect Transistors with Inorganic Gate Oxide for pH Sensing", IEEE Transactions on Electron Devices, vol. 29, No. 12, 1982, pp. 1936-1941.

Barbaro et al., "A Charge-Modulated FET for Detection of Biomolecular Processes: Conception, Modeling, and Simulation", IEEE Transactions on Electron Devices, vol. 53, No. 1, 2006, pp. 158-166.

Barbaro et al., "A CMOS, Fully Integrated Sensor for Electronic Detection of DNA Hybridization", IEEE Electronic Device Letters, vol. 27, No. 7, 2006, pp. 595-597.

Barbaro et al., "Fully electronic DNA hybridization detection by a standard CMOS biochip", Sensors and Actuators B: Chemical, vol. 118, 2006, pp. 41-46.

Bausells et al., "Ion-sensitive field-effect transistors fabricated in a commercial CMOS technology", Sensors and Actuators B: Chemical, vol. 57, Nos. 1-3, 1999, pp. 56-62.

Bergveld, "Thirty years of ISFETOLOGY What happened in the past 30 years and what may happen in the next 30 years", Sensors and Actuators B: Chemical, vol. 88, No. 1, Jan. 2003, pp. 1-20.

Chung et al., "ISFET interface circuit embedded with noise rejection capability", Electronics Letters, vol. 40, No. 18, e-pub, 2 Pages, Sep. 2, 2004, pp. 1115-1116.

Eltoukhy et al., "A 0.18um CMOS 10-6 lux bioluminescence detection system-on-chip", 2004 IEEE Intl Solid States Conference. Digest of Technical Papers. Session 12, Microsystems/12.3, Feb. 17, 2004. pp. 1-3.

EP10780934.5, Search Report, dated Jun. 12, 2015.

EP10780934.5, Extended Search Report, dated Jun. 22, 2015.

EP17185272.6, Search Report, dated Jan. 24, 2018.

Eriksson et al., "Pyrosequencing™ Technology at Elevated Temperature" Electrophoresis, vol. 25, No. 1, Jan. 2004, pp. 20-27.

Finn et al., "Towards an Optimization of FET-Based Bio-Sensors", European Cells and Materials, vol. 4, Sup 2, 2002, pp. 21-23.

Hammond et al., "A System-on-Chip Digital pH Meter for Use in a Wireless Diagnostic Capsule", IEEE Transactions on Biomedical Engineering, vol. 52, No. 4, May 2005, pp. 687-694.

Hammond et al., "Design of a Single-Chip pH Sensor Using a Conventional 0.6-.mu.m CMOS Process", IEEE Sensors Journal, vol. 4, No. 6, 2004, pp. 706-712.

Hammond et al., "Encapsulation of a liquid-sensing microchip using SU-8 photoresist", MicroElectronic Engineering, vols. 73-74, Jun. 2004, pp. 893-897.

Hammond et al., "Genomic sequencing and analysis of a Chinese Hamster ovary cell line using Illumina sequencing technology", BMC Genomics, vol. 12, No. 67, Jan. 2011, pp. 1-8.

Han "Label-free detection of biomolecules by a field-effect transistor microarray biosensor with bio-functionalized gate surfaces," Masters Dissertation, RWTH Aachen University, 2006, pp. 1-63.

Hizawa et al., "Fabrication of a two-dimensional pH image sensor using a charge transfer technique", Sensors and Actuators B: Chemical, vol. 117, No. 2, Oct. 2006, pp. 509-515.

Koch et al., "Protein detection with a novel ISFET-based zeta potential analyzer", Biosensors & Bioelectronics, vol. 14, No. 4, Apr. 1999, pp. 413-421.

Leamon et al., "Cramming More Sequencing Reactions onto Microreactor Chips", Chemical Reviews, vol. 107, No. 8, Aug. 2007, pp. 3367-3376.

Margulies et al., "Genome Sequencing in Microfabricated High-Density Picolitre Reactors", Nature, vol. 437, No. 7057, Sep. 15, 2005, pp. 376-380. (Epub Jul. 31, 2005).

Martinoia et al., "Development of ISFET Array-Based Microsystems for Bioelectrochemical measurements of cell populations", Biosensors & Bioelectronics, vol. 16, Nos. 9-12, Dec. 2001, pp. 1043-1050.

Milgrew et al., "A large transistor-based sensor array chip for direct extracellular imaging", Sensors and Actuators B: Chemical, vols. 111-112, Nov. 2005, pp. 347-353.

Milgrew et al., "The Development of Scalable Sensor Arrays Using Standard CMOS Technology", Sensors and Actuators B: Chemical, vol. 103, Nos. 1-2, Sep. 2004, pp. 37-42.

Milgrew et al., "The fabrication of scalable multi-sensor arrays using standard CMOS technology", IEEE Custom Integrated Circuits Conference, 2003, pp. 513-516.

PCT/US2010/001547, Search Report and Written Opinion, dated Aug. 5, 2010.

PCT/US2010/001543, Search Report and Written Opinion, dated Oct. 13, 2010.

PCT/US2010/001553, Search Report and Written Opinion, dated Jul. 28, 2010.

PCT/US2010/001549, Search Report and Written Opinion, dated Sep. 17, 2010.

Pourmand et al., "Direct electrical detection of DNA synthesis", Proceedings of the National Academy of Sciences, vol. 103, No. 17, Apr. 2006, pp. 6466-6470.

Purushothaman et al., "Protons and single nucleotide polymorphism detection: A simple use for the Ion Sensitive Field Effect Transistor", Sensors and Actuators B: Chemical, vol. 114, No. 2, Apr. 2006, pp. 964-968.

Purushothaman et al., "Towards Fast Solid State DNA Sequencing", IEEE ISCAS Proceedings, Circuits and Systems, vol. 4, 2002, pp. IV-169-IV-172.

Rodriguez-Villegas, "Solution to trapped charge in FGMOS transistors", Electronics Letters, vol. 39, No. 19, Oct. 2003, pp. 1416-1417.

Sakata et al., "Direct transduction of allele-specific primer extension into electrical signal using genetic field effect transistor", Biosensors & Bioelectronics, vol. 22, 2007, pp. 1311-1316.

Sakata et al., "DNA Analysis Chip Based on Field-Effect Transistors", Japanese Journal of Applied Physics, vol. 44, No. 4B, 2005, pp. 2854-2859.

Sakurai et al., "Real-Time Monitoring of DNA Polymerase Reactions by a Micro ISFET pH Sensor", Analytical Chemistry, vol. 64, No. 17, Sep. 1992, pp. 1996-1997.

Salama, "Modeling and simulation of luminescence detection platforms", Biosensors & Bioelectronics, vol. 19, No. 11, Jun. 15, 2004, pp. 1377-1386.

(56) References Cited

OTHER PUBLICATIONS

Schoning et al., "Bio FEDs (Field-Effect Devices): State-of-the-Art and New Directions", Electroanalysis, vol. 18, Nos. 19-20, Sep. 2006, pp. 1893-1900.

SG200903992-6, Search and Examination Report, dated Jan. 20, 2011, pp. 1-12.

Shepherd et al., "Towards direct biochemical analysis with weak inversion ISFETS", Intl Workshop on Biomedical, 2004, S1.5-5-S1.5-8.

Tang et al., "Polymerizing immobilization of acrylamide-modified nucleic acids and its application", Biosensors and Bioelectronics, vol. 24, No. 7, Mar. 15, 2009, 1817-1824.

Van Hal et al., "A general model to describe the electrostatic potential at electrolyte oxide interfaces", Advances in Colloid and Interface Science, vol. 69, Nos. 1-3, Dec. 1996, pp. 31-62.

Woias et al., "Slow pH response effects of silicon nitride ISFET sensors", Sensors and Actuators B: Chemical, vol. 48, Nos. 1-3, May 1998, pp. 501-504.

Woias, "Modelling the short time response of ISFET sensors", Sensors and Actuators B: Chemical, vol. 24, Nos. 1-3, Mar. 1995, pp. 211-217.

Written Opinion of the International Searching Authority for International Application No. PCT/US2010/001549 dated Sep. 17, 2010, 6 pages.

Xu et al., "Analytical Aspects of FET-Based Biosensors", Frontiers in Bioscience, vol. 10, Jan. 2005, pp. 420-430.

Yeow et al., "A very large integrated pH-ISFET sensor array chip compatible with standard CMOS processes", Sensor and Actuators B: Chemical, vol. 44, Nos. 1-3, Oct. 1997, pp. 434-440.

Yuqing et al., "Ion sensitive field effect transducer-based biosensors", Biotechnology Advances, vol. 21, No. 6, Sep. 2003, pp. 527-534.

Zhang et al., "32-Channel Full Customized CMOS Biosensor Chip for Extracellular neural Signal Recording", Proc. of the 2nd Intl. IEEE EMBs Conf. on Neural Engineering, Arlington, Virginia, Mar. 16-19, 2005, pp. v-viii.

\* cited by examiner

SCAFFOLDED NUCLEIC ACID POLYMER PARTICLES AND METHODS OF MAKING AND USING

This is a continuation of U.S. patent application Ser. No. 15/846,195 filed Dec. 18, 2017, which is a divisional of U.S. patent application Ser. No. 14/987,552 filed Jan. 4, 2016, which is a continuation of U.S. patent application Ser. No. 14/044,712 filed Oct. 3, 2013 (now U.S. Pat. No. 9,249,461), which is a continuation of U.S. patent application Ser. No. 12/785,685 filed May 24, 2010 (U.S. Pat. No. 8,574,835), which is a continuation-in-part of U.S. patent application Ser. Nos. 12/474,897 and 12/475,311 both filed May 29, 2009 (both abandoned), and claims priority under U.S. provisional application Nos. 61/242,369 filed Sep. 14, 2009; 61/263,734 filed Nov. 23, 2009; 61/291,788 filed Dec. 31, 2009; and 61/297,203 filed Jan. 21, 2010. All of the foregoing applications are incorporated by reference in their entireties.

BACKGROUND

In order to generate sufficient signal for analysis, many applications in genomics and biomedical research require the conversion of nucleic acid molecules in a library into separate, or separable, libraries of amplicons of the molecules, e.g. Margulies et al, Nature 437: 376-380 (2005); Mitra et al, Nucleic Acids Research, 27: e34 (1999); Shendure et al, Science, 309: 1728-1732 (2005); Brenner et al, Proc. Natl. Acad. Sci., 97: 1665-1670 (2000); and the like. Several techniques have been used for making such conversions, including hybrid selection (e.g., Brenner et al, cited above); in-gel polymerase chain reaction (PCR) (e.g. Mitra et al, cited above); bridge amplification (e.g. Shapero et al, Genome Research, 11: 1926-1934 (2001)); and emulsion PCR (emPCR) (e.g. Margulies et al, cited above). Most of these techniques employ particulate supports, such as beads, which spatially concentrate the amplicons for enhanced signal-to-noise ratios, as well as other benefits, such as, better reagent access.

These techniques have several drawbacks. In some cases, amplicons are either in a planar format (e.g. Mitra et al, cited above; Adessi et al, Nucleic Acids Research, 28: e87 (2000)), which limits ease of manipulation and/or reagent access, or the amplicons are on bead surfaces, which lack sufficient fragment density or concentration for adequate signal-to-noise ratios. In other cases, amplifications must be done in emulsions in order to obtain clonal populations of templates. Such emulsion reactions are labor intensive and require a high degree of expertise, which significantly increases costs. It would be very useful if supports were available which were capable of providing a higher density of analyte binding or attachment sites, particularly for clonal populations of nucleic acid fragments. It would also be advantageous if such supports did not require emulsion reactions for producing clonal populations.

Gels have been widely used as supports in analytical and synthetic processes and as encapsulating agents, e.g. Weaver et al, U.S. Pat. No. 5,055,390; Trnovsky et al, U.S. Pat. No. 6,586,176, and have interiors accessible to analytical reagents. However, such particulates are limited in that they are typically produced with widely varying size distributions, particularly at lower size ranges, e.g. less than about 30 µm, which makes them unsuitable for many exacting analytical applications, such as large scale DNA sequencing.

It would be highly useful if methods and compositions were available for creating small-sized monodisperse populations of gel-based particulate supports, which could be readily loaded with analytes, such as amplicons of nucleic acid fragments.

SUMMARY OF THE INVENTION

The present invention is generally directed to particle compositions for nucleic acid analysis, which address the aforementioned issues with current methodologies, as well as other related issues. The present invention is exemplified in a number of implementations and applications, some of which are summarized below and throughout the specification.

In one aspect, the invention includes the production and use of porous microparticles for increasing the number of polynucleotides templates within a defined volume. In one embodiment such porous microparticles comprise three-dimensional scaffolds for attaching greater numbers of template molecules than possible with solid beads that have only a two-dimensional surface available for attachment. In one embodiment, such porous microparticles are referred to herein as nucleic acid polymer particles.

In another embodiment, such porous microparticles comprise particles having shapes with larger surface to volume ratios than spherical particles. Such shapes include tubes, shells, hollow spheres with accessible interiors (e.g. nanocapsules), barrels, multiply connected solids, including doubly connected solids, such as donut-shaped solids and their topological equivalents, triply connected solids and their topological equivalents, four-way connected solids and their topologically equivalents, and the like. Such porous microparticles are referred to herein as "non-spheroidal microparticles." Techniques for producing and characterizing such particles are disclosed in Elaissari, editor, Colloidal Polymers: Synthesis and Characterization (Marcel Dekker, Inc., New York, 2003), and like references.

In another aspect the invention provides a composition of nucleic acid polymer particles each comprising polynucleotides attached to a non-nucleosidic polymer network, each such polymer network having a volume and the polynucleotides being attached to the polymer network throughout its volume, wherein the number of attached polynucleotides is at least $6.9 \times 10^4$ per $\mu m^3$ and wherein the oligonucleotides have an average nearest neighbor distance of 22 nm or less. In one aspect, the polynucleotide is a DNA fragment in the range of from 100 to 500 nucleotides in length, or in the range of from 100 to 200 nucleotides in length. In another aspect, such polynucleotide is a double stranded DNA (dsDNA) having a length in the range of from 150 to 250 basepairs.

In another aspect, the invention provides amplicon libraries, such libraries comprising a plurality of amplicons, each amplicon comprising a clonal population of a single polynucleotide from a nucleic acid library, each polynucleotide of the clonal population being attached to a non-nucleosidic polymer network, each such polymer network having a volume and the polynucleotides of the clonal population being attached to the polymer network throughout its volume, wherein the number of attached polynucleotides is at least $6.9 \times 10^4$ per $\mu m^3$. In another aspect, polynucleotides of such amplicons have an average nearest neighbor distance of 22 nm or less, or an average nearest neighbor distance of 20 nm or less. In still another aspect, such polynucleotides are each a double stranded DNA (dsDNA) having a length in the range of from 150 to 250 basepairs, or a length in the range of from 150 to 200 basepairs.

In one aspect, an amplicon library of the invention comprises a plurality of amplicons, each amplicon comprising a clonal population of a single polynucleotide from a nucleic acid library, each polynucleotide of the clonal population being attached to a non-nucleosidic polymer network, each such polymer network having a volume and the polynucleotides of the clonal population being attached to the polymer network throughout its volume, wherein the number of attached polynucleotides is at least $6.9 \times 10^4$ per $\mu m^3$. In one embodiment, a plurality of amplicons is in the range of from $10^4$ to $10^7$ amplicons.

In another aspect, the invention provides methods of making monodisperse populations of gel particles by combining a monodisperse emulsion of a gel reaction mixture without an initiator and an emulsion with a dispersed phase containing an initiator or a continuous phase solution saturated with an initiator. In one embodiment, volumes of the gel particles of such monodisperse populations have coefficients of variation of less than fifteen percent, or in another embodiment, less than twelve percent.

In another aspect, the invention provides a method of making amplicon libraries comprising the steps: (a) combining in an amplification reaction mixture a library of polynucleotide fragments each having at least one primer binding site and a population of non-nucleosidic polymer networks, each such polymer network having a volume of less than $1.4 \times 10^4$ $\mu m^3$ and having primers attached thereto, and the volumes of the non-nucleosidic polymer networks having a coefficient of variation of fifteen percent or less; (b) performing an amplification reaction so that primers of the polymer networks are each extended along a polynucleotide fragment annealed thereto so that clonal populations of such polynucleotide fragments are formed on the polymer networks, thereby forming an amplicon library. In one embodiment, the method of making amplicon libraries further includes a step of enriching polymer networks having clonal populations of polynucleotide fragments attached by separating them from polymer networks without such fragments. In another embodiment, such separation is accomplished by affinity separation or by electrophoretic separation.

In still another aspect, the invention includes methods of using monodisperse gel particle compositions to make amplicon libraries without an emulsion reaction.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the present invention.

BRIEF DESCRIPTIONS OF THE DRAWINGS

FIGS. 1A and 1B illustrate the presence of nucleic acid polymer particles inside microwells of a semiconductor sequencing device and the effects of different polymer network sizes within a library.

FIG. 2A schematically illustrates production of spheroidal gel particles by membrane emulsification using a micromachined membrane and continuous polymerization by heat.

FIG. 2B schematically illustrates another embodiment for producing spheroidal gel particles by membrane emulsification and batch mode polymerization by heat.

FIG. 3 diagrammatically illustrates a bridge PCR on a surface.

FIG. 4 diagrammatically illustrates bridge PCR on a suspension of nucleic acid polymer particles.

DETAILED DESCRIPTION OF THE INVENTION

Figure 1A:
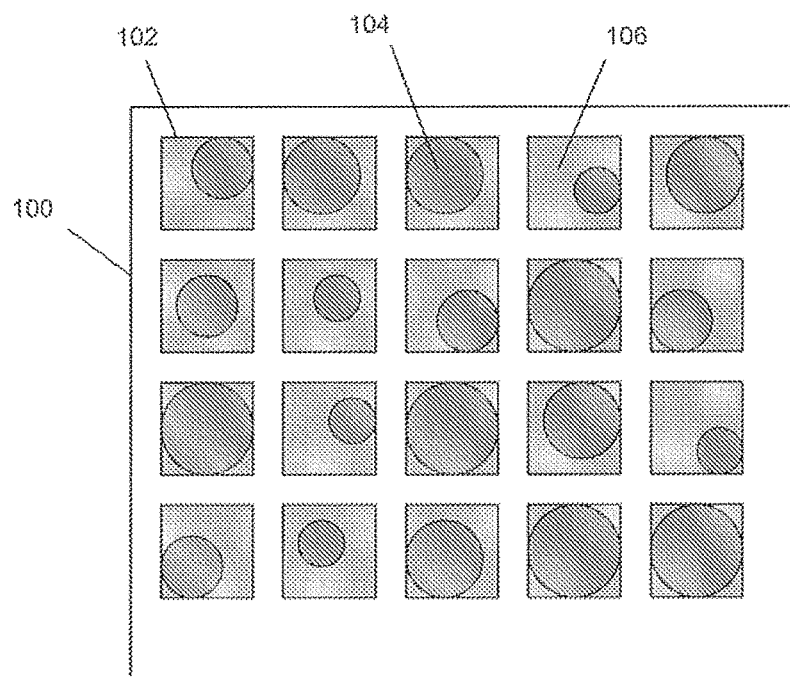

The practice of the present invention may employ, unless otherwise indicated, conventional techniques and descriptions of organic chemistry, molecular biology (including recombinant techniques), cell biology, and biochemistry, which are within the skill of the art. Such conventional techniques include, but are not limited to, preparation of synthetic polynucleotides, polymerization techniques, chemical and physical analysis of polymer particles, nucleic acid sequencing and analysis, and the like. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *PCR Primer: A Laboratory Manual, and Molecular Cloning: A Laboratory Manual* (all from Cold Spring Harbor Laboratory Press), Hermanson, Bioconjugate Techniques, Second Edition (Academic Press, 2008); Merkus, Particle Size Measurements (Springer, 2009); Rubinstein and Colby, Polymer Physics (Oxford University Press, 2003); and the like.

The invention is directed to methods and compositions for enhancing the sensitivity of nucleic acid analysis, particularly where many different nucleic acid fragments are assayed simultaneously, such as in large-scale parallel DNA sequencing reactions. In one aspect, the compositions of the invention result from the conversion of a library of individual nucleic acid fragments into a library of individual solid phase amplicons that provide higher concentrations of fragments per amplicon and greater uniformity of amplicon size than current methodologies. Solid phase amplicons of the invention are composite materials made up of a framework, or scaffold, of a hydrophilic covalent non-nucleosidic polymer (referred to herein as a "polymer network" or as a "porous microparticle") and covalently attached copies of usually one kind of nucleic acid fragment, or in some embodiments, two kinds of nucleic acid fragment. In some preferred embodiments, such nucleic acid fragment is a nucleic acid primer. In other preferred embodiments, such nucleic acid fragment is a DNA fragment from a library, which may have been formed on a polymer network by extension of a covalently attached primer. (In such embodiments, it is understood that a single "kind" in this case, may include unextended primers or partially extended primers, which have different lengths but otherwise identical sequences). Such solid phase amplicons are synonymously referred to as "scaffolded nucleic acid polymer particles" or simply "nucleic acid polymer particles." Compositions of the invention include libraries or collections of such solid phase amplicons, or equivalently, nucleic acid polymer particles. In one aspect, the invention includes compositions comprising populations of such solid phase amplicons. In one aspect, polymer networks are stable in a wide pH range, e.g. from 4 to 10, and especially from 6 to 9, and they are chemically and physically stable in physiological salt solutions and/or electrolytes. Likewise, polymer networks are preferably inert to reactants, reagents and/or reaction conditions and buffers used in analytical assays and reactions for nucleic acids, including, but not limited to, polymerase reactions, ligase reactions, nuclease reactions, polymerase chain reactions, and the like. Polymer networks are preferably chemically and physically stable over a wide temperature range, e.g. 0° C. to 100° C., and 5° C. to 95° C. In one aspect, polymer networks are substantially nonswelling in under a wide range of reaction conditions, particularly polymerase extension reaction conditions. In one aspect, by substantially nonswelling, it is meant that the volume of a polymer network changes by no more than five percent within a temperature range of from 25° C. to 70° C. and under chemical conditions of physiological or assay salt and pH in the range of from 6 to 10, and especially in the range of from 7 to 9. In one aspect, the porosity of polymer networks permits free or substantially free diffusion of proteins having a size in the range of from 50 to 200 kilodaltons, or from 50 to 150 kilodaltons, or from 50 to 125 kilodaltons. In another aspect, the porosity of polymer networks permits free or substantially free diffusion of nucleic acid polymerases. In various embodiments, such porosity may be selected to permit free or substantially free diffusion of primers and/or a DNA polymerase, including but not limited to, a Taq polymerase, a 9° N polymerase, an *E. coli* DNA polymerase I, a T7 DNA polymerase, a Bsu DNA polymerase, a Klenow fragment DNA polymerase, a Phusion DNA polymerase, a Vent DNA polymerase, a Bst DNA polymerase, a phi29 DNA polymerase, a T4 DNA polymerase, or the like. In another embodiment, polymer networks have a porosity that renders them permeable to proteins having a size in the range of from 50 to 200 kilodaltons, or from 50 to 150 kilodaltons, or from 50 to 125 kilodaltons. In one embodiment, the porosity of polymer networks is selected so that such permeability is at least fifty percent of the diffusability in polymer-free solution, or at least twenty-five percent of such diffusability, or at least ten percent of such diffusability. In another aspect, polymer networks have an average pore size in the range of from 20 to 200 nm in diameter, or from 25 to 100 nm in diameter, or from 30 to 100 nm in diameter.

In another aspect, polymer networks may have empty channels or hollow cores that when taken together with the polymer network volume comprise at least 10%, at least 20%, at least 30%, at least 40%, at least 50%, at least 60%, at least 70%, at least 80%, at least 90% of the combined volume.

In another aspect, nucleic acid fragments are uniformly attached throughout the volume of polymer networks. In some embodiments, nucleic acid fragments are uniformly and randomly attached throughout the volume of polymer networks (i.e. as approximately a Poisson distribution). In yet other embodiments, nucleic acid fragments may be attached throughout a layer or portion of a polymer network. In further embodiments, nucleic acid fragments may be attached non-uniformly throughout the volume of polymer networks. For example, in spherically shaped polymer networks, a concentration of attached nucleic acid fragments may be a function of distance from the center of such polymer network. In one such embodiment, such function describes a monotonically decreasing concentration from the surface of a polymer network to its center.

The density of nucleic acids may be expressed in terms of expected or average nearest neighbor distance, which allows surface densities to be compared with volume densities. Equivalent densities of nucleic acids distributed throughout a spheroidal volume have larger expected nearest neighbor distances than those of nucleic acids distributed on the surface of such a volume. Expected nearest neighbor distances for Poisson distributed points or molecules are readily computed for surfaces or volumes, e.g. Pielou, Introduction to Mathematical Ecology (Wiley-Interscience, New York, 1977). Since large molecules or molecular complexes of interest (e.g. template-primer-polymerase complexes) have volumes roughly in the range of from 1000 to $1.2 \times 10^5$ nm$^3$ (Holmes et al, Electrophoresis, 12: 253-263 (1991)), higher concentrations of such can be achieved by attaching them throughout a volume rather than on a surface. In one aspect, nucleic acid polymer particles of the invention have 150 to 200 basepair nucleic acids immobilized throughout a spheroidal volume having a diameter in the range of from 0.5 to 10 μm in an approximate Poisson distribution having an expected nearest neighbor distance in the range of from 15 to 22 nm. In another aspect, such spheroidal volume has a diameter in the range of from 1 to 10 μm and such Poisson distribution of dsDNAs has an expected nearest neighbor distance in the range of from 18 to 20 nm.

Figure 1B:
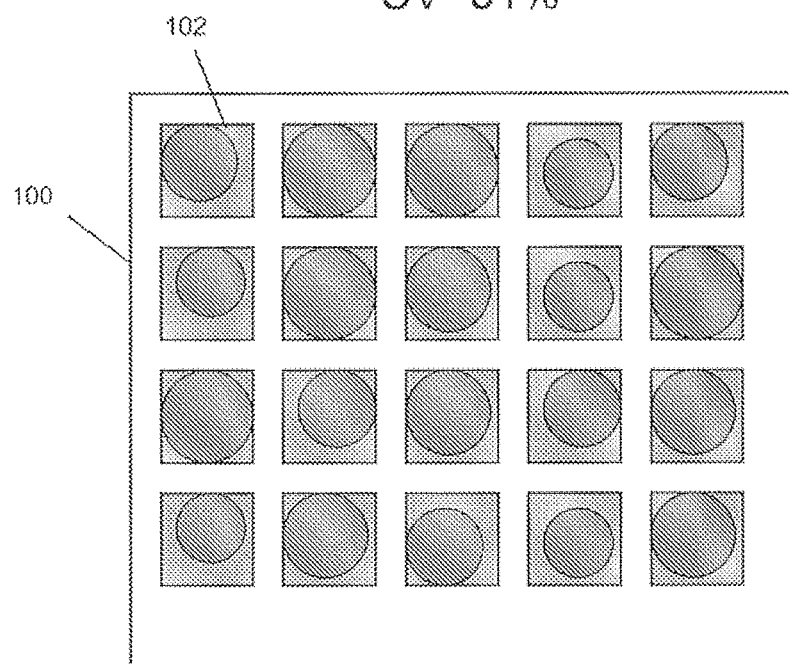

Polymer networks may have a variety of shapes, including but not limited to, spherical, cylindrical, barrel shaped, toroidal, conical, tubular, hemispherical, cubical, and topological equivalents of the foregoing. In one aspect, polymer networks are spherically shaped, which are readily obtained from emulsion-based methods of making them. An important application of nucleic acid polymer particle compositions is their use in massively parallel sequencing reactions where nucleic acids attached to the polymer networks making up such particles are derived from fragments of a target polynucleotide of interest, such as a genome. In several large scale sequencing approaches, clonal populations of fragments, usually attached to separate beads, are subjected to sequencing reactions in microwells, or equivalent enclosures, e.g. as disclosed in Rothberg et al, U.S. patent publication 2009/0127589; Gamal et al, U.S. Pat. No. 7,595,883; Leamon et al, U.S. Pat. No. 7,323,305; and the like. In particular, approaches based on making electrochemical measurements, such as Rothberg et al (cited above), benefit from populations of nucleic acid polymer particles that have low coefficients of variation. For example, FIGS. 1A and 1B illustrate top views of ISFET sensor arrays (100), e.g. as disclosed in Rothberg et al (cited above), which include a rectilinear array of microwells (102) filled with microparticles (104) and electrolyte (106). In FIG. 1A, the coefficient of variation of the diameters of microparticles (104) is 51%, and in FIG. 1B the corresponding coefficient of variation is 22%. Whenever electrical measurements are made through or across the microwells, differences in microparticle sizes and motions give rise to resistive noise; thus, the greater the coefficient of variation in microparticle size, the greater the noise. Generally, if the coefficient of variation of the size of a particle is large, several difficulties can arise: (i) flows of reagents across the beads or particles may dislodge and wash away some particles, e.g small particles or particles too large to completely fit into a microwell, (ii) in the case of ion-based sequencing approaches, such as pH-based sequencing disclosed in Rothberg et al (cited above), fluid noise sensed by a electronic-based sensor will vary depending on the fluid gap around the particle in the well, and (iii)

signals generated by reactions taking place on the nucleic acids of a particle will vary with the size of the particle, which adds a signal processing complication because many sequencing chemistries generate a signal that depends on the number of bases incorporated in a polymerase extension reaction. As a consequence, it is advantageous to have populations of nucleic acid polymer particles with sizes, e.g. volumes, or diameters for spherical particles, which have a low coefficient of variation. In one aspect, such populations of particles have volumes with coefficients of variation less than 25 percent; and in further aspects, such populations of particles have volumes with coefficients of variation less than 20 percent; and in further aspects, such populations of particles have volumes with coefficients of variation less than 15 percent; and in further aspects, such populations of particles have volumes with coefficients of variation less than 10 percent; or less than 5 percent. Preferably, populations of spherical polymer networks have coefficients of variation less than 15 percent, and more preferably, less than 10 percent, or less than 5 percent.

In another aspect, spherical polymer networks have average sizes (diameters) less than 30 µm, or in the range of from 0.5 µm to 30 µm, or in the range of from 0.5 µm to 15 µm, or in the range of from 0.5 µm to 10 µm.

In some embodiments, the porous microparticle is hollow (i.e., it has a hollow core); while in other embodiments it has a porous core.

As mentioned above, an aspect of the invention includes amplicon libraries comprising a plurality of solid phase amplicons each, in turn, comprising nucleic acid polymer particles each having a clonal population of polynucleotides, such as genomic fragments, attached throughout the volume of a polymer network.

Compositions

Polymer networks may be made of a wide variety of components and the method of manufacturing may vary widely. Design factors for making polymer networks include, but are not limited to, the following: (i) the polymers of the networks are hydrophilic, (ii) they are capable of having a pore and/or network structure (e.g. average pore diameter, tortuosity, and the like) that permits interior access to various enzymes, especially polymerases, (iii) they are physically and chemically stable under conditions where biomolecules, such as enzymes, are functional and they are substantially non-swelling under the same conditions. There is a great amount of guidance in the art for selecting polymers and polymerization methodologies to produce polymer networks meeting such performance criteria, such as the following exemplary references, which are incorporated by reference: Saltzman and Langer, J. Biophys., 55:163 (1989); Ghosh et al, U.S. Pat. No. 5,478,893; Mirzabekov, U.S. Pat. No. 6,656,725; Johnson et al, U.S. Pat. No. 6,372,813; Tang and Xiao, Biosensors and Bioelectronics, 24: 1817-1824 (2009); Boles et al, U.S. Pat. Nos. 5,932,711 and 6,180,770; Xiao et al, Electrophoresis, 28: 1903-1912 (2007); Holmes et al, Electrophoresis, 12: 253-263 (1991); Shapero et al, Genome Research, 11: 1926-1934 (2001); Righetti et al, J. Biochem. Biophys. Methods, 4: 347-363 (1981); Mitra et al, Nucleic Acids Research, 27: e34 (1999); Rehman et al, Nucleic Acids Research, 27: 649-655 (1999); Smith, U.S. Pat. No. 4,485,224; Chiari et al, U.S. Pat. No. 5,785,832; Rickwood and Hames, Editors, Gel Electrophoresis of Nucleic Acids (IRL Press, Oxford, 1982); Chrambach, The Practice of Quantitative Gel Electrophoresis (VCH, Deerfield Beach, 1985); Mitra et al, Anal. Biochem., 320: 55-65 (2003); Kenney et al, Biotechniques, 25: 516 (1998); Elaissari, editor, Colloidal Polymers: Synthesis and Characterization (Marcel Dekker, Inc., New York, 2003); and the like.

In one aspect, polymer networks comprise polymers selected from the following group: agarose; polyoxybutylene; diethylacrylamide; polyoxyethylene; polyacrylamide; polyoxypropylene; N,N-polydimethylacrylamide; poly(N-isopropylacrylamide); polyvinylpyrrolidone; poly-N-hydroxyacrylamide; and the like. As described more fully below, such polymers may be formed into polymer networks using conventional methodologies, e.g. cross-linking methods, methods for producing desired shapes, and the like.

In some embodiments, the nucleic acids are bound to polymer networks with one or more non-nucleic acid polymers or linking groups. In some embodiments, the non-nucleic acid polymers are polyethylene glycol (PEG) polymers. The PEG polymers may be of varying lengths. In some embodiments, the non-nucleic acid polymers are dextran polymers and/or chitosan polymers. In some embodiments, the non-nucleic acid polymers include PEG polymers and dextran polymers. In some embodiments, the non-nucleic acid polymers include PEG polymers and chitosan polymers. The non-nucleic acid polymers may be linear or branched. Still other methods for attaching nucleic acids to beads are taught by Lund et al., Nucleic Acids Research, 1988, 16(22):10861-10880, Joos et al. Anal Biochem, 1997, 247:96-101, Steinberg et al. Biopolymers, 2004, 73:597-605, and Steinberg-Tatman et al. Bioconjugate Chem 2006 17:841-848.

In one embodiment, nucleic acid polymer particles are made by first making polymer networks that incorporate either bromoacetyl groups or alternative thiol groups, then reacting either a thiol derivatized oligonucleotide or a bromoacetyl-derivatized oligonucleotide respectively, as taught by Ghosh et al, U.S. Pat. No. 5,478,893, which is incorporated by reference. Synthesizing bromoacetyl-derivatized and thiol-derivatized oligonucleotides is further disclosed by Gryaznov, U.S. Pat. No. 5,830,658, which is incorporated by reference. In one aspect, polyacrylamide particles are employed that may be size selected either before or after bromoacetyl- and thiol-derivatized components are reacted.

In another embodiment, nucleic acid polymer particles are made by preparing a polymer network that incorporates a click chemistry functionality then combining it with oligonucleotides having a complementary click chemistry functionality, so that rapid and specific bonds are formed and a nucleic acid polymer particle results. Click chemistry functionalities and reactions are well-known and are disclosed in the following references, which are incorporated by reference: Lahann, editor, Click Chemistry for Biotechnology and Material Science (Wiley, 2009); Kolb et al, Angew. Chem. Int. Ed., 40: 2004-2021 (2001); Binder et al, Macromolecular Rapid Comm., 28: 15-54 (2007); Sharpless et al, U.S. Pat. No. 7,375,234; Carell et al, U.S. patent publication 2009/0215635; and the like. Reagents containing click chemistry reactive functionalities and complementary functionalities are commercially available from Glen Research (Sterling, Va.); Sigma Aldrich (St. Louis, Mo.), baseclick GmbH (Tutzing, Germany); and like companies. In one aspect, the click chemistry reactive functionality is an azide and the click chemistry complementary functionality is an alkyne. In one embodiment, a reaction between such functionalities is catalyzed by copper(I). In another aspect, a click chemistry reactive functionality or complementary functionality is incorporated into a polyacrylamide polymer matrix.

Of particular interest are polymer networks comprising polyacrylamide gels. Polyacrylamide gels are formed by copolymerization of acrylamide and bis-acrylamide ("bis," N,N'-methylene-bisacrylamide). The reaction is a vinyl addition polymerization initiated by a free radical-generating system. Polymerization is initiated by ammonium persulfate and TEMED (tetramethylethylenediamine): TEMED accelerates the rate of formation of free radicals from persulfate and these in turn catalyze polymerization. The persulfate free radicals convert acrylamide monomers to free radicals which react with unactivated monomers to begin the polymerization chain reaction. The elongating polymer chains are randomly crosslinked by bis, resulting in a gel with a characteristic porosity which depends on the polymerization conditions and monomer concentrations. Riboflavin (or riboflavin-5'-phosphate) may also be used as a source of free radicals, often in combination with TEMED and ammonium persulfate. In the presence of light and oxygen, riboflavin is converted to its leuco form, which is active in initiating polymerization, which is usually referred to as photochemical polymerization. In a standard nomenclature for forming polyacrylamide gels, T represents the total percentage concentration (w/v, in mg/mL) of monomer (acrylamide plus crosslinker) in the gel. The term C refers to the percentage of the total monomer represented by the crosslinker. For example, an 8%, 19:1 (acrylamide/bisacrylamide) gel would have a T value of 8% and a C value of 5%.

In one aspect, polymer networks comprise polyacrylamide gels with total monomer percentages in the range of from 3-20 percent, and more preferably, in the range of from 5 to 10 percent. In one embodiment, crosslinker percentage of monomers is in the range of from 5 to 10 percent. In a particular embodiment, polymer networks comprise 10 percent total acrylamide of which 10 percent is bisacrylamide.

Accordingly, in one aspect, the invention includes a polyacrylamide particle composition comprising a population of polyacrylamide particles with an average particle size of less than 15 μm with a coefficient of variation of less than 15 percent. In one embodiment, the polyacrylamide particles have a weight:volume percentage of twenty-five percent or less. In another embodiment, the polyacrylamide particles are spheroidal and have an average diameter of less than 15 μm with a coefficient of variation of less than 15 percent.

Methods of Making Nucleic Acid Polymer Particles

Nucleic acid polymer particles of the invention may be made by a wide variety of methods. In one aspect, such method include steps of (i) forming a reaction mixture whose polymerization may be controlled by physical conditions, e.g. heat, or the addition of a catalyst; (ii) performing a polymerization reaction to produce polymer networks or candidate polymer networks or nucleic acid polymer particles or candidate polymer particles depending on reactants and conditions employed, and (iii) optionally, selecting candidate polymer networks or candidate nucleic acid polymer particles in a predetermined size range. Nucleic acid polymer particles may be made by first making polymer networks followed by attachment of polynucleotides, or they may be made by co-polymerization of oligonucleotide components along with monomers and crosslinkers. In addition to the chemical processes that determine the composition of polymer networks and nucleic acid polymer particles, physical process are employed to create such networks and particles with desired shapes and size distributions. Such physical processes include, but are not limited to, flow focusing using microfluidics devices, e.g. Nisisako et al, LabChip, 8: 287-293 (2008); Kumaresan et al, Anal. Chem., 80: 3522-3529 (2008), pneumatic disruption of a sheath-sample flow stream, e.g. Lin et al, Biomed Microdevices, 9: 833-843 (2007); sieving, molding, e.g. Rolland et al, J. Am. Chem. Soc., 127: 10096-10100 (2005), sonication, controlled shearing, and membrane emulsion. Further exemplary references include the following: Mak et al. Adv. Funct. Mater. 2008 18:2930-2937; Morimoto et al. MEMS 2008 Tucson Ariz. USA Jan. 13-17, 2008 Poster Abstract 304-307; Lee et al. Adv. Mater. 2008 20:3498-3503; Martin-Banderas et al. Small. 2005 1(7):688-92; and published PCT application WO03/078659. Of particular interest are the following three methods of forming polymer networks.

UV polymerization. Polymer networks may be made by polymerization of acrylamide spray droplets generated by single or multiple nozzles located on an oscillating membrane, such as in a commercially available system from The Technology Partnership (www.ttp.com) which sprays droplets from single or multiple nozzles located on a stainless steel membrane by piezo electronically actuating the membrane and allowing it to oscillate at its natural resonance frequency. This yields monodispersed droplets in a gaseous atmosphere (such as Argon) at rates of tens of thousands to millions of droplets per second. These droplets are then streamed passed a strong UV light source for photoinitiated polymerization.

Polymerization with molding. This approach involves the molding of a paste which disperses the acrylamide, bisacrylamide and acrydite labeled oligonucleotides in a sacrificial "porogen" followed by, but not limited to, photoinitiated radical polymerization of the acrylamide monomers with subsequent removal of the porogen my dissolution and repeated washing. The molding technology is available through Liquidia Technologies (Research Triangle Park, N.C.) and disclosed in DeSimone et al, PCT publication WO 2007/024323, and like references. Such approached are particularly useful for producing non-spheroidal microparticles in defined shapes, such as tetrahedral shapes, hemispherical shapes, barrel shapes, open capsular shapes, toroidal shapes, tube shapes, and the like, which have greater surface areas than spheroidal shaped particles with the same solid volume. Preferably, the areas of the non-spheroidal microparticles in a composition are substantially the same. In one aspect, substantially the same in reference to non-spheroidal microparticles means that the areas of the microparticles in a composition have a coefficient of variation of less than 15 percent, or less than 10 percent, or less than 5 percent. In one embodiment, non-spherical microparticles of the invention have at least twice the surface area of a sphere with equal volume, or preferably, at least three times the surface area, or at least four time the surface area, or at least five times the surface area. In another embodiment, non-spheroidal microparticles are composed of polyacrylamide gel. In still another embodiment such polyacrylamide gel is made using acryldite oligonucleotides so that the resulting non-spheroidal microparicles have covalently attached oligonucleotides, which may be used as primers in extension reactions, ligation reactions, amplification reactions, or the like. Alternatively, oligonucleotides or other reagents, such as antibodies, may be attached by using linking groups and chemistries known in the art, such as described above. In further preference, non-spheroidal microparticles are compact in that they may be closely enclosed within a microwell or other reaction chamber. In one embodiment, non-spheroidal microparticles of the invention may be enclosed by a sphere having a volume twice that of the non-spheroidal microparticle, or a volume three times that of such microparticle, or four time that of such microparticle. In another embodiment, non-spheroidal microparticles of the invention are enclosed by a cylinder having a diameter:height aspect ratio of 1:1.5 and a diameter of 10 µm, or 5 µm, or 2 µm, or a cylinder having a diameter:height aspect ratio of 1:1 and a diameter of 10 µm, or 5 µm, or 2 µm, or 1 µm.

Membrane emulsification. Polymerization of emulsified acrylamide requires a) control of particle size distribution during polymerization, and b) a controllable polymerization method. Control of size distribution requires both the minimization of polydispersity due to the emulsification process as well as minimization of instability of the emulsion leading to coalescence of individual drops prior to polymerization. Highly monodisperse emulsions may be achieved through microsieve emulsification techniques (such as provided commercially by Nanomi B.V., The Netherlands) and disclosed the following exemplary references: Wissink et al, PCT publication WO2005/115599; Nakajima et al, U.S. Pat. No. 6,155,710; Qiu et al, U.S. Pat. No. 7,307,104; Gijsbertsen-Abrahase, "Membrane emulsification: process principles," (Ph.D. Thesis, Wageningen Universiteit, 2003); Geerken, "Emulsification with micro-engineered devices", Ph.D. Thesis, University of Twente, ISBN: 90-365-2432-6, 1974; Yuan, et. al., "Manufacture of controlled emulsions and particulates using membrane emulsification", Desalination, 224, 2008; Geerken, et. al., "Interfacial aspects of water drop formation at micro-engineered orifices", Journal of Colloid and Interface Science, 312, 2007; Sotoyama, et. al., "Water/Oil emulsions prepared by the membrane emulsification method and their stability", Journal of Food Science, Vol. 64, No 2, 1999; Kosvintsev, et. al., "Membrane emulsification: Droplet size and uniformity in the absence of surface shear", Journal of Membrane Science, 313, 2008; Egidi, et. al., "Membrane emulsification using membranes of regular pore spacing: Droplet size and uniformity in the presence of surface shear", Journal of Membrane Science, 323, 2008; Abrahamse, et. al., "Analysis of droplet formation and interactions during cross-flow membrane emulsification", Journal of Membrane Science, 204, 2002; Katoh, et. al., "Preparation of food emulsions using a membrane emulsification system", Journal of Membrane Science, 113, 1996; Charcosset, et. al., "The membrane emulsification process—a review", Journal of Chemical Technology and Biotechnology, 79, 209-218, 2004; and the like.

In membrane-based emulsification to produce particles, a discontinuous phase (aqueous solution of monomers and other components) is extruded through a plate with multiple through holes where the other side of the plate is constantly washed with a stream of continuous phase (oil formulation with surfactant) such that the droplets that break off from the individual orifices are carried away by a stream of continuous phase. The droplet stream is then passed through a heated section of tubing which will initiate the polymerization and is finally collected in bulk for extraction of the polymer particles.

Figure 2A:
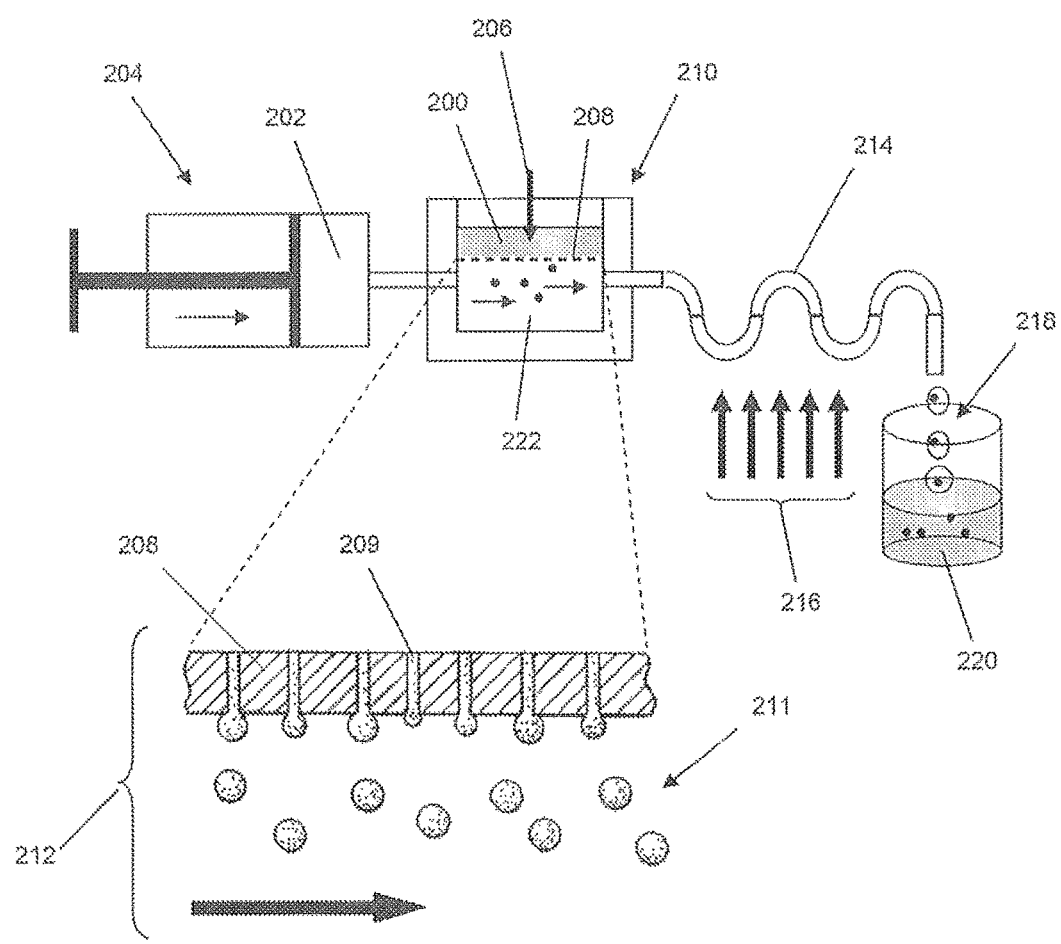

FIG. 2A illustrates apparatus in one approach to membrane emulsification. Aqueous phase gel reaction mixture (200) is passed through membrane (208) held in reaction vessel (210). Membrane (208) has pores or orifices (209) that create droplets (211) of a predetermined size (as shown in expanded view (212)) dispersed in an immiscible continuous phase fluid (202). As droplets (211) are formed, slowly flowing continuous phase (222) sweeps them away from membrane (208) to tubing (214) where (in this embodiment) droplets (211) are polymerized by applying heat (216). The flow of continuous phase (202) may be controlled by syringe pump (204). The length and diameter of tubing (214) is selected to correspond to the amount of time required for polymerization given the amount of heat applied. Polymerized droplets (218) are deposited in collection vessel (220), after which they are removed and washed to remove traces of continuous phase (202). The volume of the aqueous phase gel reaction mixture (200) is a relatively small (200 ul-5 ml) and is pumped at low flow rates (200 uL/hr to 1 mL/hr) such that the rate of droplet formation at each orifice (209) is about 2-20 drops/second. A syringe pump or gravity flow may be used for this purpose. Continuous phase (202), an oil/surfactant formulation is a much larger volume, e.g. 100-1000× greater than the aqueous flow. A large syringe pump (204) or pressure driven flow (pneumatic) may be used to control its flow and volume. In this embodiment, as mentioned above, the stream containing an emulsion of aqueous drops in oil/surfactant formulation passing through tubing (214) is passed through a heated section of tubing (the I.D. of the tubing may be increased to reduce the linear flow rate, backpressure and increase the residence time in the heated section. The polymerized particles are finally collected in collection vessel (220) for extraction of the polymer particles.

In one aspect, membrane (208) is microfabricated, e.g. from a silicon substrate, using conventional micromachining techniques described in the above references. Typically, the diameters of orifices (209) are 25 to 35 percent of the expected diameters of particles (211). It is important that the aqueous solution (200) does not wet the membrane surfaces, particularly in and/or at the orifices so that the droplets or micelles entering the continuous phase have a quick break off from the rest of the aqueous phase.

In another aspect, droplets of gel reaction mixture (less initiator) may be formed then polymerized by exposure to initiator and heat in a batch mode by at least the following methods. In particular, monodisperse polyacrylamide particles may be made by first producing an emulsion with monodisperse droplets of polyacrylamide reaction mixture without an initiator followed by combining with either a second emulsion with an initiator in the disperse phase or a continuous phase (equivalent to that of the first emulsion) saturated with an initiator. Method 1. A monodisperse emulsion is mixed with a micro or macro emulsion of initiator in the same oil/surfactant system. The initiator emulsion is generated rapidly by vortexing or using an Ultra Turrax, or like immiscible phase fluid. Since the monomers are soluble in the continuous phase polymerization of monomer in the initiator emulsion has been observed. Method 2. An initiator soluble in the continuous phase is used to initiate the polymerization in a previously generated emulsion. Use of oil-soluble initiators is well-known in the art as evidenced by the following references, which are incorporated by references: Alduncin et al, Macromolecules, 27: 2256-2261 (1994); Capek, Adv. Colloid and Interface Science, 91: 295-334 (2001); Gromov et al, Vysokomol. Soyed. A30: 1164-1168 (1988); U.S. Pat. No. 3,284,393. The pre-made emulsion is simply diluted with a saturated solution of initiator (for example, a 1:1 ratio of emulsion to initiator solution in a polyacrylamide system) and heated to a temperature up to or below 96° C. In one aspect of making polyacrylamide nucleic acid polymer particles, the emulsion is heated to 90° C. for 2 h. Alternatively a water soluble initiator can be used which will not require the dilution of the emulsion, or the oil used during the formation of the monodisperse emulsion can be saturated with an appropriate initiator. For method 1, only water soluble initiators would be used which includes azo type compounds as well as inorganic peroxides. Exemplary initiators include ammonium persulfate, hydroxymethanesulfinic acid monosodium salt dihydrate, potassium persulfate, sodium persulfate, and the like. For methods 2. both water soluble (in dispersed phase) or oil soluble initiators may be used. Example of each are given below in Tables I and II. Note: The temperature at which the initiator has a half-life of 10 h is given. The lower the temperature the more reactive the initiator. Selection of appropriately reactive initiator allows one of ordinary skill in the art to tune the rate at which the polymerization is initiated and what maximum temperatures are used during the reaction.

Figure 2B:
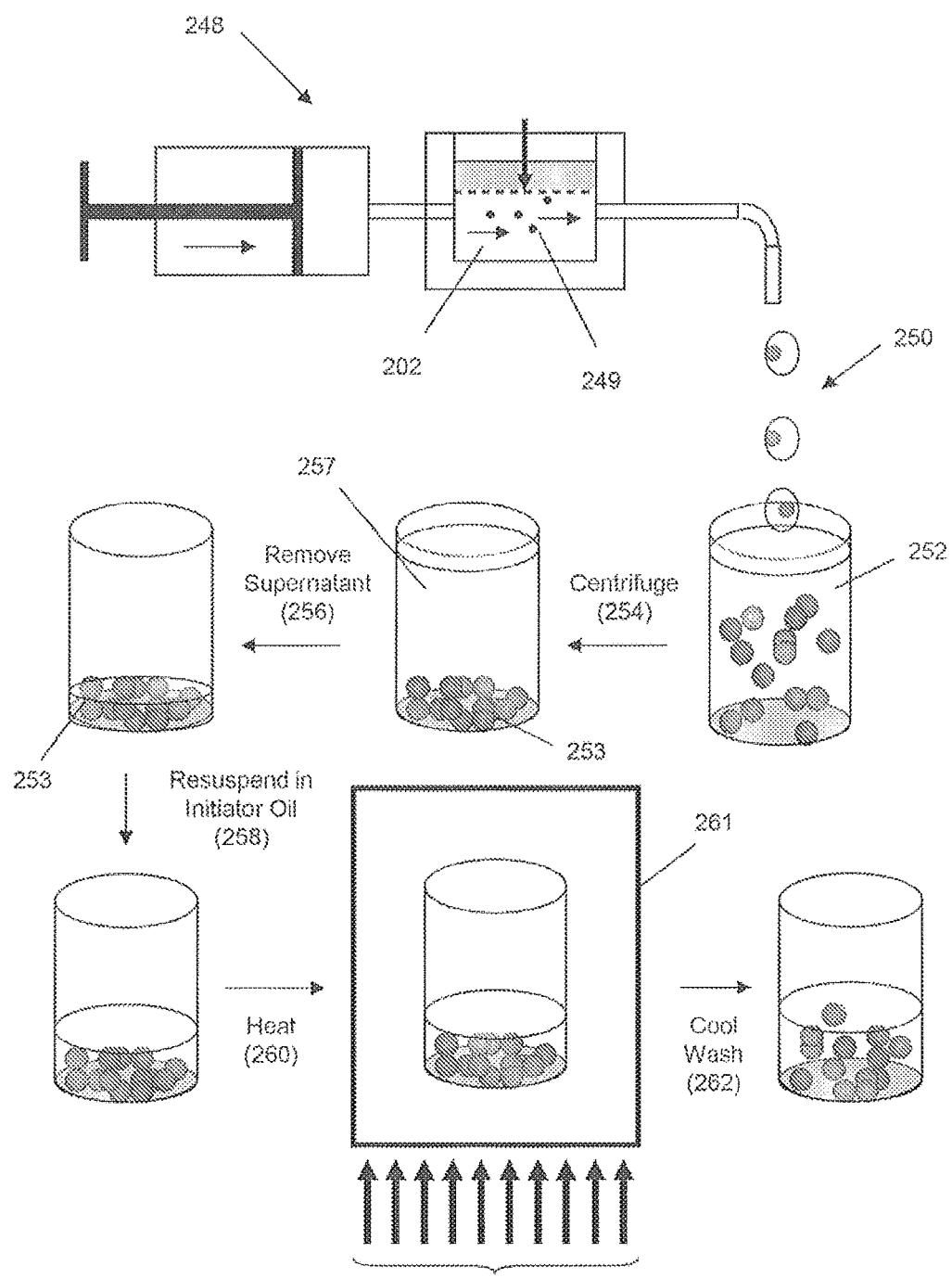

This approach is illustrated in FIG. 2B. Nucleic acid polymer particles may be made in a batch-mode process where a polymerization initiator is introduced after droplets of gel reaction mixture are formed. A similar membrane emulsion apparatus (248) as described in FIG. 2A is used to generate spheroidal droplets of gel reaction mixture (249) in an immiscible continuous phase (202), except that gel reaction mixture in this embodiment does not contain a polymerization initiator. After leaving apparatus (248), continuous phase and droplets (250) are placed in tube (252), after which the mixture is centrifuged (254) to drive droplets (255) to the bottom of the tube and supernatant (257) comprising the continuous phase is removed (256). Droplets (253) are then resuspended (258) in continuous phase fluid that contains a suitable initiator, after which the mixture is immediately placed (260) in oven (261) where it is heated to drive the polymerization reaction. After polymerization is complete, the mixture is cooled and washed (262) several times to remove the continuous phase material from the resulting nucleic acid polymer particles.

In one aspect, the invention include a method of making nucleic acid polymer particles comprising the following steps: (a) combining in a reaction mixture hydrophilic monomers each having at least one reactive functionality and at least one complementary functionality and hydrophilic cross-linkers each having at least two of either the reactive functionality or complementary functionality, (i) wherein the reactive functionality and complementary functionality are capable of reacting with one another under catalytic conditions to form covalent linkages, (ii) wherein a proportion of the monomer have an ancillary functionality or an oligonucleotide attached, the ancillary functionality being capable of reacting with a capture moiety without cross reacting with the reactive functionality or the complementary functionality, and (iii) wherein concentrations of the monomers and cross-linkers, and the proportion of monomers having an ancillary functionality or oligonucleotide in the reaction mixture are selected so that a cross-linked polymer is capable of forming that has a density of oligonucleotides or ancillary functionalities of at least $1 \times 10^5$ per $\mu m^3$ and an average pore size in the range of from 20 to 150 nm; (b) passing the reaction mixture through a porous membrane into a non-aqueous phase so that spherical droplets of reaction mixture are dispersed into the non-aqueous phase; and (c) subjecting the spherical droplets of the reaction mixture to catalytic conditions so that polymer networks are formed. Ancillary functionalities include monomer derivatives that include reactive groups such as thiol or bromoacetyl groups disclosed by Ghosh et al (cited above), groups comprising one of a pair of click chemistry reactants, or the like In one aspect, the porous membrane comprises a silicon membrane having a plurality of identical orifices through which the reaction mixture passes. In another aspect, the method includes a further step of removing the polymer networks from said non-aqueous phase and washing the polymer networks. In one embodiment, the hydrophilic monomer is an acrylamide and the hydrophilic cross-linker is an N,N'-methylenebisacylamide. In another embodiment, a proportion of the hydrophilic monomer is an acrydite oligonucleotide.

In another aspect, the invention includes a method of making monodisperse populations of polyacrylamide particles comprising the step of combining a monodisperse emulsion of a polyacrylamide reaction mixture without an initiator and an emulsion with a dispersed phase containing an initiator or a continuous phase solution saturated with an initiator. In one embodiment such reaction mixture includes a nucleic acid acrydite monomer.

TABLE I

Water Soluble Azo Initiator Compounds

| Structure | 10 hour half-life decomposition temperature |
|---|---|
| [structure] | 44° C. |
| [structure] | 47° C. |
| [structure] | 56° C. |
| [structure] | 57° C. |
| [structure] | 60° C. |
| [structure] | 61° C. |
| [structure] | 67° C. |

TABLE I-continued

Water Soluble Azo Initiator Compounds

| Structure | 10 hour half-life decomposition temperature |
|---|---|
| HOH₂C–C(=O)–C(CH₃)(CH₃)–N=N–C(CH₃)(CH₃)–C(=O)–CH₂OH with HOH₂CHCHN and NHCHCH₂OH, HOH₂C and CH₂OH branches | 80° C. |
| HOH₂CH₂CHN–C(=O)–C(CH₃)(CH₃)–N=N–C(CH₃)(CH₃)–C(=O)–NHCH₂CH₂OH | 87° C. |

TABLE II

Oil Soluble Azo Initiator Compounds

| Structure | 10 hour half-life decomposition temperature |
|---|---|
| H₃CO–C(H₃C)(CH₂CH₃)–C(CH₃)(CN)–N=N–C(CN)(CH₃)–C(CH₃)(CH₂CH₃)–OCH₃ | 30° C. |
| H₃CHCH₂C(H₃C)–C(CH₃)(CN)–N=N–C(CN)(CH₃)–CH₂CHCH₃(CH₃) | 51° C. |
| H₃CO–C(=O)–C(CH₃)(CH₃)–N=N–C(CH₃)(CH₃)–C(=O)–OCH₃ | 66° C. |
| H₃CH₂C–C(CH₃)(CN)–N=N–C(CN)(CH₃)–CH₂CH₃ | 67° C. |
| (cyclohexyl)(CN)C–N=N–C(CN)(cyclohexyl) | 88° C. |
| H₂C=HCH₂CHN–C(=O)–C(CH₃)(CH₃)–N=N–C(CH₃)(CH₃)–C(=O)–NHCH₂CH=CH₂ | 96° C. |
| H₃C–C(CH₃)(CN)–N=N–CONH₂ | 104° C. |
| H₃CH₂CH₂CH₂CHN–C(=O)–C(CH₃)(CH₃)–N=N–C(CH₃)(CH₃)–C(=O)–NHCH₂CH₂CH₂CH₃ | 110° C. |

TABLE II-continued

Oil Soluble Azo Initiator Compounds

| Structure | 10 hour half-life decomposition temperature |
|---|---|
| (structure shown) | 111° C. |

Measuring Size Distributions of Nucleic Acid Polymer Particles

In one aspect, size distributions of bulk manufactured polymer networks and/or nucleic acid polymer particles are controlled so that their coefficients of variation are as small as possible. For such control, it is important to be able to conveniently measure the sizes of a sample of candidate particles to determine whether their populations have appropriate coefficients of variation. Many techniques are available for making such measurements, including laser diffraction, flow cytometry, coulter counting, image analysis, acoustical spectroscopy, and the like. Instruments for laser diffraction are commercially available, e.g. Malvern Instruments (Malvern, United Kingdom); instruments for flow analysis are commercially available from Becton Dickinson (San Jose, Calif.); Image analysis systems and software are widely available commercially, e.g. Becton Dickinson, Biolmaging Systems (Rockville, Md.). The foregoing techniques for characterizing particles are disclosed in Dukhin and Goetz, Ultrasound for Characterizing Colloids (Elsevier Science, 2002); Elaissari, editor, Colloidal Polymers: Synthesis and Characterization (Marcel Dekker, Inc., New York, 2003); Shapiro, Practical Flow Cytometry, 4$^{th}$ edition (Wiley-Liss, 2003); and like references. In the case of polymer networks comprising polyacrylamide, fluorescent monomers are available that may be added to gel reaction mixtures for incorporation into the polymer networks to aid in their tracking and sizing, e.g. U.S. Pat. No. 5,043,406.

Making Amplicon Libraries With Nucleic Acid Polymer Particles

Nucleic acid polymer particles of the invention are particularly useful in multiplex genetic assays, including analysis of single nucleotide polymorphisms, DNA sequencing, and the like, where polynucleotide analytes, i.e. target polynucleotides, in a sample must be amplified in the course of analysis. Such analytical techniques use a wide variety of amplification methodologies which can be used with nucleic acid polymer particles of the invention, including, but not limited to, emulsion PCR (emPCR), bridge amplification, NASBA, rolling circle amplification, and the like. Exemplary references disclosing such techniques are described in the following references, which are incorporated by reference: Marguiles et al, Nature, 437: 376-380 (2005); Adams et al, U.S. Pat. No. 5,641,658; Boles et al, U.S. Pat. No. 6,300,070; Berka et al, U.S. patent publication 2005/0079510; Shapero et al (cited above); and the like.

Figure 3:
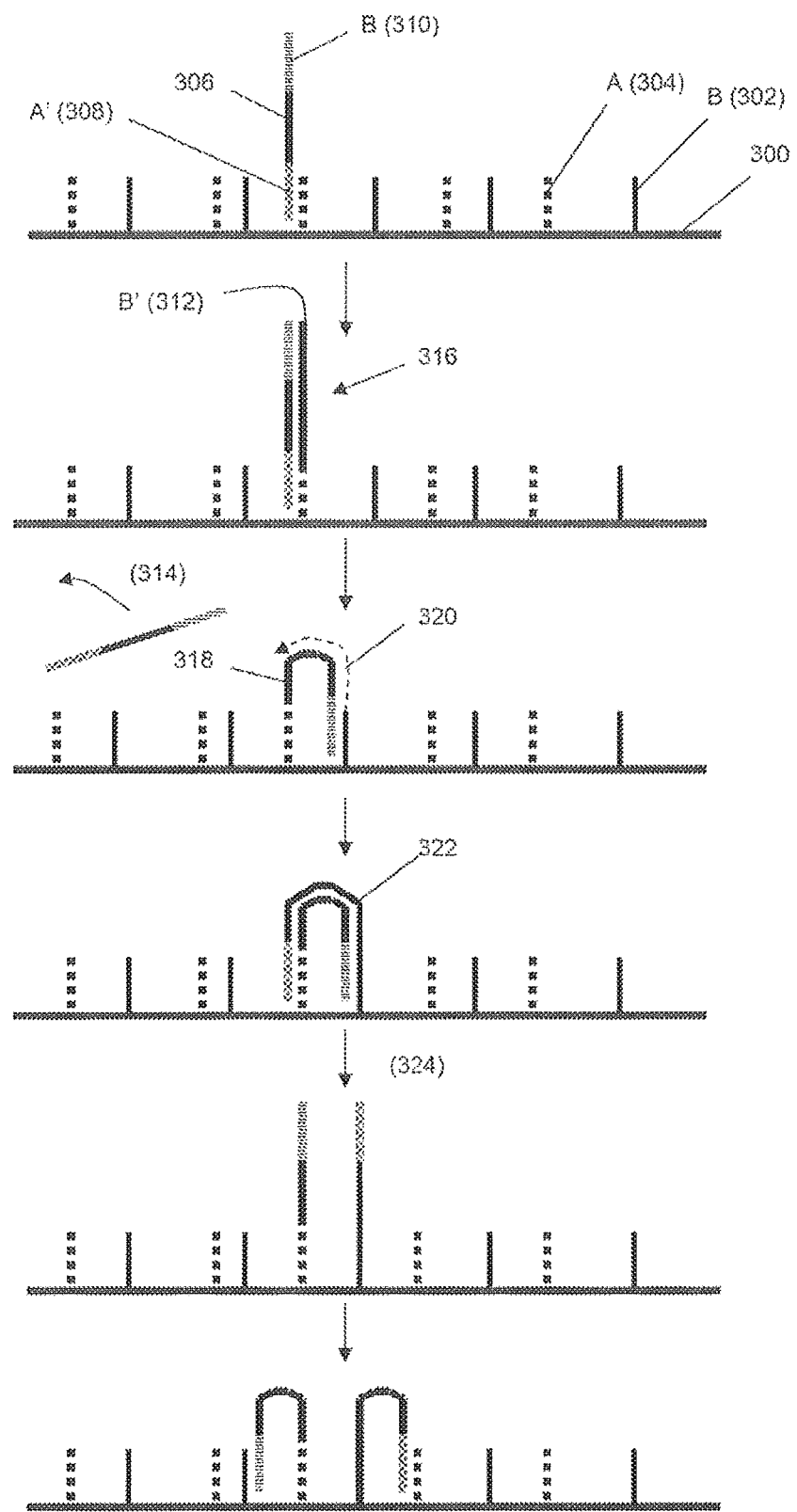

Bridge PCR amplification on surfaces is described in Adessi et al (cited above) and in Boles et al, U.S. Pat. No. 6,300,070, which is incorporated by reference. Briefly, the technique is illustrated in FIG. 3. A substrate (300) is provided that has attached via their 5' ends at least two primer sequences, A (302) and B (304). Template (306) having 3' primer binding site A' (308) (that is complementary to A) and primer sequence B (310) (that has the same sequence as B on surface (300)) anneals to a primer A on surface (300) so that primer A may be extended, e.g. by a polymerase, along template (306) to produce double stranded product (316). Template (306) is melted off (314) leaving single stranded extention product (318) attached to surface (300). Conditions are applied so that single stranded extension product (318) anneals to an adjacent primer B (302) on surface (300) so that such primer B may be extended (320) to form extension product (322). After melting, extension products (318) and (322) are available (324) for additional cycles of annealing and extension which form populations of extension products having identical sequences to (318) and (322). In some embodiments, one of primers A and B may have a scissile linkage for its removal to obtain a single population on surface (300).

Figure 4:
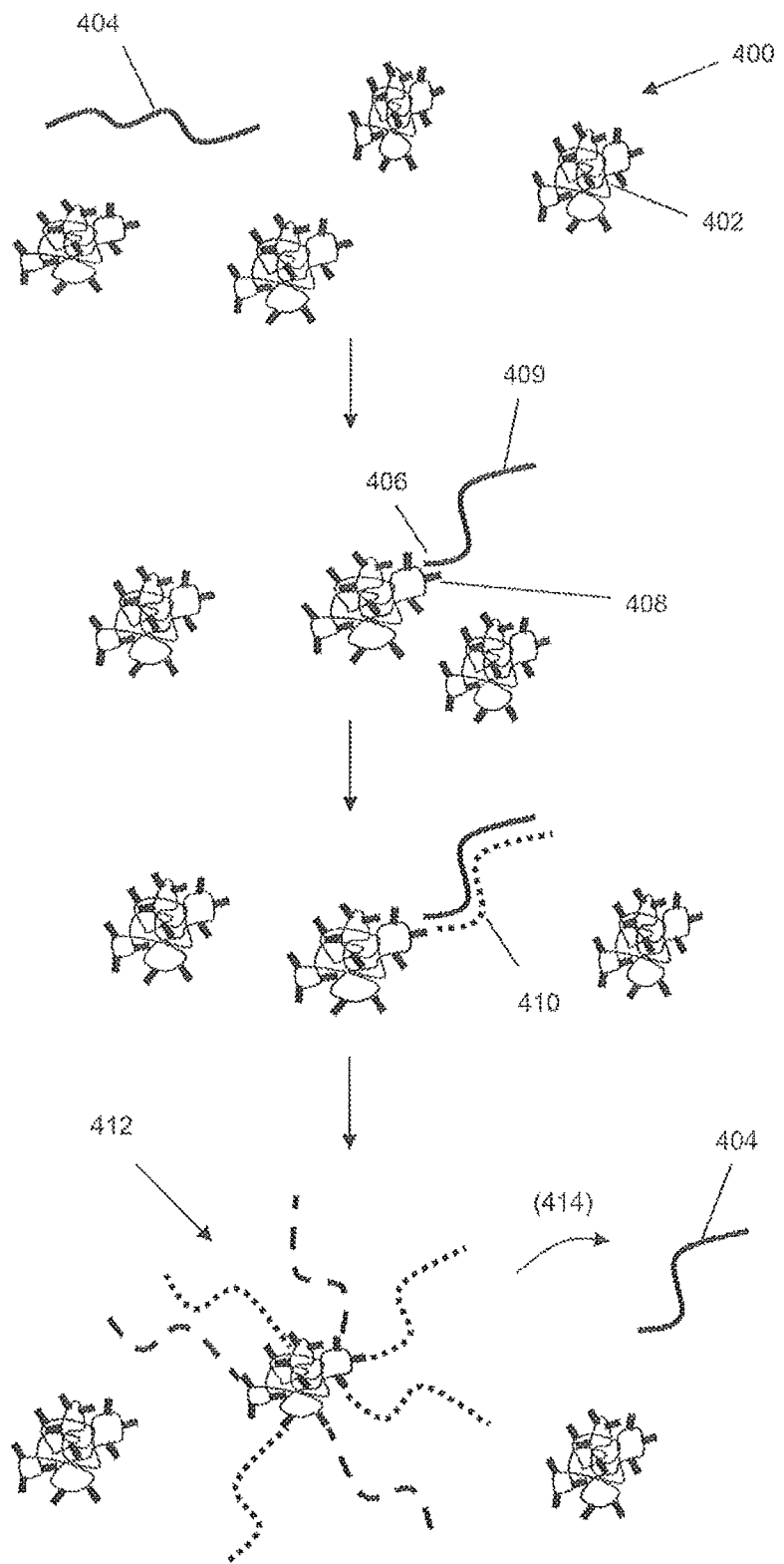
Figure 5:
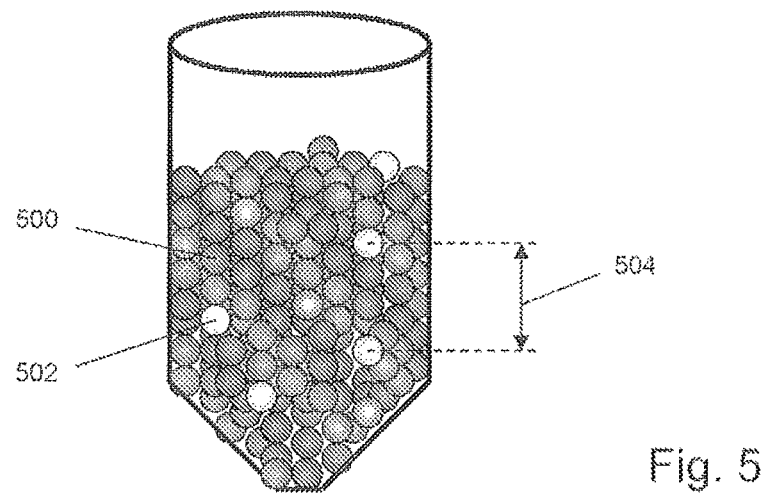
FIG. 5 illustrates a method of minimizing cross-contamination of bridge PCR templates among closely packed particles.

In accordance with a method of the invention, a bridge PCR may be performed on nucleic acid polymer particles described herein. The method may be employed to make amplicon libraries without the use of emulsion reactions. As illustrated in FIG. 4, suspension (400) of nucleic acid polymer particles (402) is combined with template (404), the latter being in a very dilute concentration relative to the concentration of nucleic acid polymer particles, so that the probability of two different templates annealing to the same nucleic acid polymer particle is very low. On a molar basis, for example, nucleic acid polymer particle may be present at 10 times, or 100 times the concentration of template. As in FIG. 3, template (404) has primer binding region at its 5' end (406) that is complementary to one (408) of two primers on the nucleic acid polymer particles and a sequence at its 3' end (409) identical to that of the other primer on the nucleic acid polymer particles. After template (404) anneals to primer (408), primer (408) is extended to form extension product (410), after which template (404) is melted and released (414). Extension product (410) may then anneal to other primers on the nucleic acid polymer particle to form additional extension products and eventually a bi-clonal population (412) of templates and its complement in reverse orientation. As released template (404) may participate in further amplifications on other nucleic acid polymer particles, preferably the spacing or concentration of such particles is controlled to reduce the probability that such an event occurs (which otherwise may cross contaminate another particle with a second template amplicon). In particular, whenever handling or operations result in nucleic acid polymer particles settling out of solution, a closely packed mass of particles forms, which could facilitate such cross contamination. As illustrated in FIG. 5, this may be prevented or reduced by including inert spacer particles (500) along with nucleic acid polymer particles (502). In one embodiment, the number and size of spacing particles (500) may be selected to control expected distance (504) between nucleic acid polymer particles (502). In another embodiment, for nucleic acid polymer particles and spacer particles of approximately the same size, a ratio of spacer particle to nucleic acid polymer particle is 10:1, or 100:1, or 1000:1. Spacer particles may also be selected that are smaller in size than nucleic acid polymer particles so that interstitial spaces between them have smaller cross sections and create longer diffusion paths. In one embodiment, spacer particles may be swellable so that interstitial spaces are reduced or eliminated upon swelling. Spacer particles may also contain tethered nucleases for digesting released or unused surplus templates that remain in the reaction solution. Compositions and techniques for making selecting and making spacer particles with covalently attached or trapped nucleases are described in Hermanson, Bioconjugate Techniques, $2^{nd}$ edition (Academic Press); and like references.

In one aspect, the invention provides a method of making an amplicon library comprising the steps of: (a) combining in a polymerase chain reaction mixture a library of polynucleotide fragments each having a first primer binding site at one end and a second primer binding site at the other end, and a population of nucleic acid polymer particles each comprising a non-nucleosidic polymer network having attached thereto a first primer and a second primer each at a concentration of at least $1\times10^5$ primers per $\mu m^3$ such that each polynucleotide fragment is capable of annealing to a first primer by its first primer binding site and to a second primer by a complement of its second primer binding site; and (b) performing a polymerase chain reaction in the presence of a quantity of spacer particles so that primers of the polymer networks are extended along polynucleotide fragments annealed thereto so that clonal populations of complements of such polynucleotide fragments are formed on the polymer networks, thereby forming an amplicon library, the quantity of spacer particles being selected to prevent cross-contamination of amplicons. In one aspect, the polymer networks each have a volume and a concentration of the polynucleotide fragments and a concentration of said polymer networks are selected so that in said step of combining at least 10 percent of said polymer networks have at a single said polynucleotide fragment within its volume. For some embodiments, the non-nucleosidic polymer network has a volume of less than $1.4\times10^4$ $\mu m^3$.

In still another aspect, the invention provides a method of making an amplicon library by performing a bridge polymerase chain reaction on a composition of monodisperse nucleic acid polymer particles. In an embodiment of such method the composition of monodisperse nucleic acid polymer particles includes a quantity of spacer particles.

Figure 7:
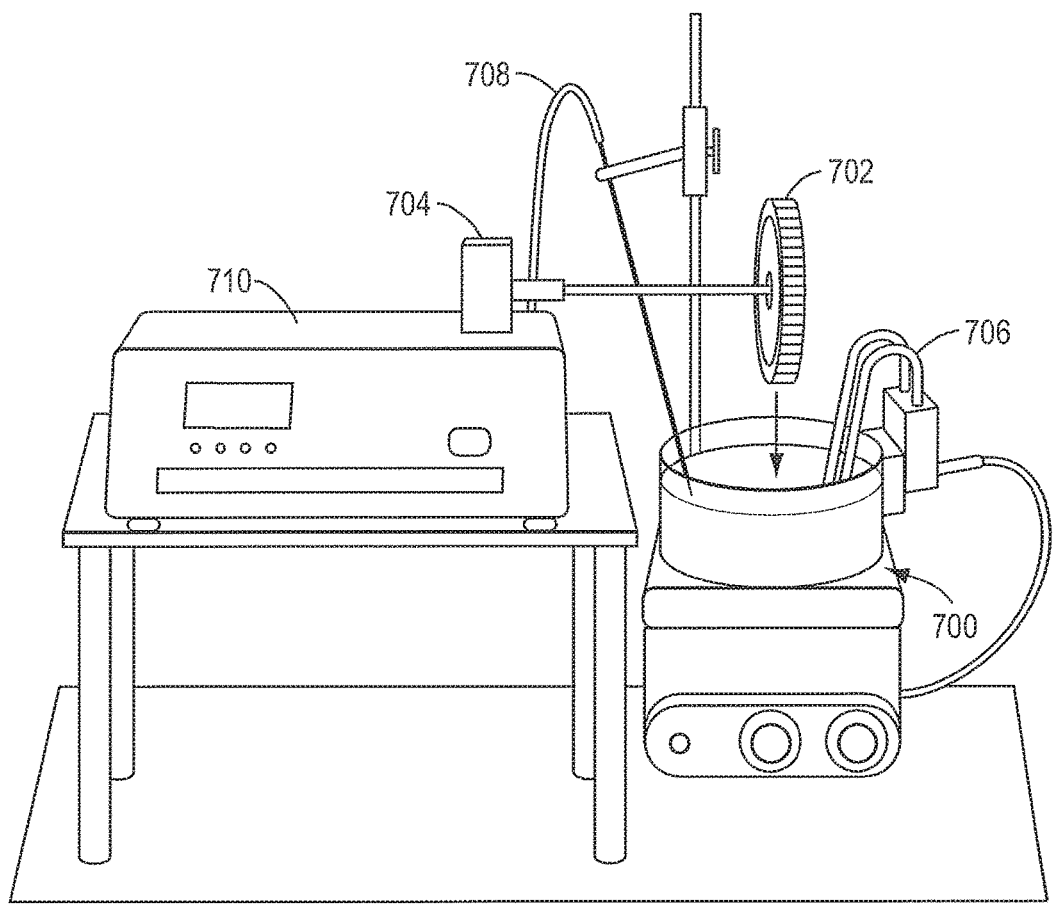
FIG. 7 shows a simple thermocycler for carrying out PCRs while preventing porous particles from settling at the bottom of a reaction vessel.

Alternatively, nucleic acid polymer particles being used in bridge PCR may be amplified in a thermocycler instrument that provides agitation or rotation of the reaction chambers or tubes to present settling or prolonged particle-particle contact. A simple device shown in FIG. 7 may be used as such a thermocycler. Reaction tubes (not shown) are placed in holders near the outer periphery of wheel (702) which may be lowered into heated oil bath (700) and rotated by motor (704). Wheel (702) rotates at a predetermined speed and depth in oil bath (700), whose temperature is controlled by controller (710) by way of thermometer (708) and heater (706). By programming controller (710) a thermocycler is provided, which ensures that nucleic acid polymer particles do not settle during amplification.

Methods of making amplicon libraries may also include a step of enriching nucleic acid polymer particles having clonal populations of polynucleotide fragments. In one embodiment, such enrichment may be accomplished by affinity purification, for example, by annealing an oligonucleotide with a capture moiety, such as biotin, to a primer binding site of the polynucleotide fragments, after which the resulting complexes may be captured, e.g. by streptavidinated magnetic beads, and separated from particles without polynucleotide fragments. In another embodiment, nucleic acid polymer particles having clonal populations of polynucleotide fragments may be separated from particles without polynucleotide fragments by electrophoresis, e.g. using a commercially available instrument (such as, PippinPrep automated prep gel system, Sage Science, Beverly, Mass.).

Figure 6:
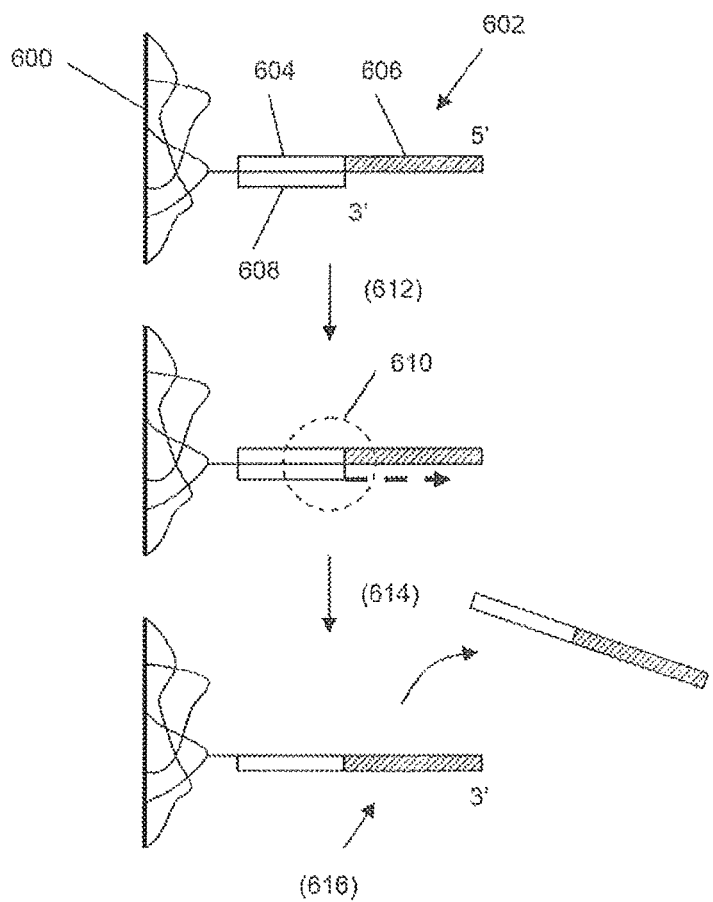
FIG. 6 illustrates a method of using adaptor oligonucleotides to allow one kind of nucleic acid polymer particle to be used to capture and amplify a selected set of nucleic acids, such as particular exons of one or more genes.

Nucleic acid polymer particles may further be used in analysis of selected sets of genes or other polynucleotide sequences. Sets of such particles with specificities for particular predetermined polynucleotide targets are readily prepared from a single batch of particles using the technique outlined in FIG. 6. To a batch of nucleic acid polymer particles (600) that have the same primers (608) attached by their 5' ends, is annealed adaptor oligonucleotide (602) that comprises 3' end (604) that is complementary to primer (608) and that includes 5' end (606) which has a sequence identical to a target polynucleotide to be captured and amplified. After such annealing, polymerase (610) is added in a conventional polymerase reaction mixture so that primer (608) is extended along 5' end of oligonucleotide (602) as a template. After such extension (614), oligonucleotide (602) is released to leave sequence-specific primer (616) on nucleic acid polymer particle (600). In the same reaction (by providing oligonucleotide (602) as a mixture of A and B primers) or in a subsequent reaction, the same steps may be followed to add a second primer for bridge amplification on the resulting set of nucleic acid polymer particles. Alternatively, primer (608) (or a second primer) may be extended in a template-driven ligation reaction, where a 5' phosphorylated oligonucleotide (not shown) complementary to 5' segment (606) is provided. This technique may be used to prepare a set of nucleic acid polymer particles containing a plurality of particles each with a different specificity. Such a set may be used to selectively amplify a predetermined set of target polynucleotides in a bridge PCR for analysis.

Nucleic Acid Sequencing with Nucleic Acid Polymer Particles

Figure 8:
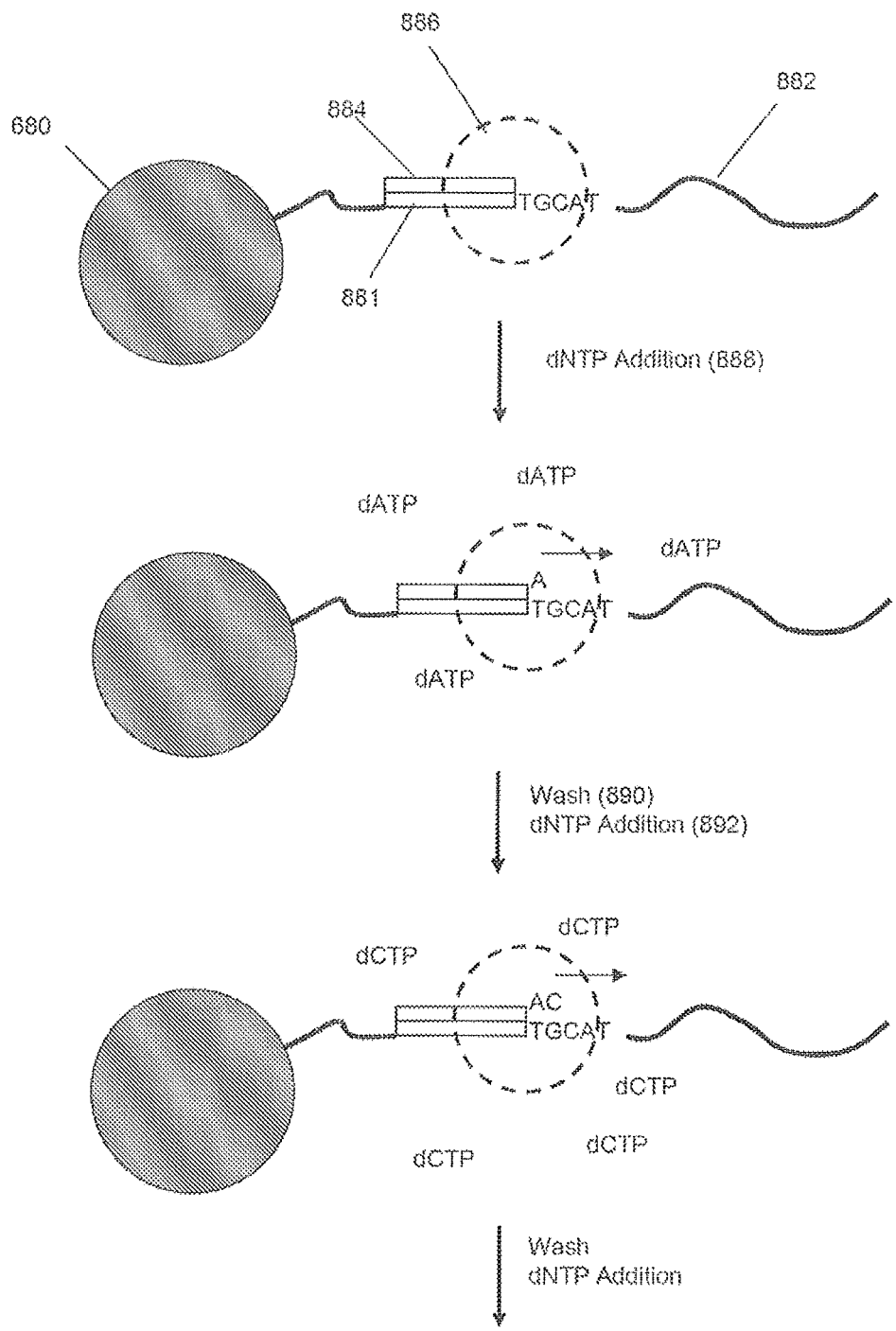
FIG. 8 illustrates steps of a nucleic acid sequencing method using nucleic acid polymer particles of the invention.

In one aspect, the invention may be used for carrying out label-free DNA sequencing, and in particular, pH-based DNA sequencing. The concept of label-free DNA sequencing, including pH-based DNA sequencing, has been described in the literature, including the following references that are incorporated by reference: Rothberg et al, U.S. patent publication 2009/0026082; Anderson et al, Sensors and Actuators B Chem., 129: 79-86 (2008); Pourmand et al, Proc. Natl. Acad. Sci., 103: 6466-6470 (2006); and the like. Briefly, in pH-based DNA sequencing, base incorporations are determined by measuring hydrogen ions that are generated as natural byproducts of polymerase-catalyzed extension reactions. Nucleic acid polymer particles are used advantageously in pH-based sequencing because greater concentrations of templates may be attached to them thereby increasing the signal-to-noise ratio of the pH signal associated with base incorporations. Nucleic acid polymer particles are used to make amplicon libraries as described above which, in turn, are used with apparatus as described in Rothberg et al (cited above). In one embodiment, templates each having a primer and polymerase operably bound are loaded into reaction chambers (such as the microwells disclosed in Rothberg et al, cited above), after which repeated cycles of deoxynucleoside triphosphate (dNTP) addition and washing are carried out. In some embodiments, such templates may be attached as clonal populations to a solid support, such as a microparticle, bead, or the like, and such clonal populations are loaded into reaction chambers. For example, templates may be prepared as disclosed in U.S. Pat. No. 7,323,305, which is incorporated by reference. As used herein, "operably bound" means that a primer is annealed to a template so that the primer's 3' end may be extended by a polymerase and that a polymerase is bound to such primer-template duplex, or in close proximity thereof so that binding and/or extension takes place whenever dNTPs are added. In each addition step of the cycle, the polymerase extends the primer by incorporating added dNTP only if the next base in the template is the complement of the added dNTP. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the reaction chamber. The production of hydrogen ions is monotonically related to the number of contiguous complementary bases in the template (as well as the total number of template molecules with primer and polymerase that participate in an extension reaction). Thus, when there is a number of contiguous identical complementary bases in the template (i.e. a homopolymer region), the number of hydrogen ions generated, and therefore the magnitude of the local pH change, is proportional to the number of contiguous identical complementary bases. (The corresponding output signals are sometimes referred to as "1-mer", "2-mer", "3-mer" output signals, and so on). If the next base in the template is not complementary to the added dNTP, then no incorporation occurs and no hydrogen ion is released (in which case, the output signal is sometimes referred to as a "0-mer" output signal.) In each wash step of the cycle, an unbuffered wash solution at a predetermined pH is used to remove the dNTP of the previous step in order to prevent misincorporations in later cycles. Usually, the four different kinds of dNTP are added sequentially to the reaction chambers, so that each reaction is exposed to the four different dNTPs one at a time, such as in the following sequence: dATP, dCTP, dGTP, dTTP, dATP, dCTP, dGTP, dTTP, and so on, with each exposure followed by a wash step. The process is illustrated in FIG. 8 for template (882) with primer binding site (881) attached to nucleic acid polymer particle (880). Primer (884) and DNA polymerase (886) operably bound to template (882). Upon the addition (888) of dNTP (shown as dATP), polymerase (886) incorporates a nucleotide since "T" is the next nucleotide in template (882). Wash step (890) follows, after which the next dNTP (dCTP) is added (892). Optionally, after each step of adding a dNTP, an additional step may be performed wherein the reaction chambers are treated with a dNTP-destroying agent, such as apyrase, to eliminate any residual dNTPs remaining in the chamber, which may result in spurious extensions in subsequent cycles.

In one embodiment, a sequencing method exemplified in FIG. 8 may be carry out using the apparatus of the invention in the following steps: (a) disposing a plurality of template nucleic acids into a plurality of reaction chambers disposed on a sensor array, the sensor array comprising a plurality of sensors and each reaction chamber being disposed on and in a sensing relationship with at least one sensor configured to provide at least one output signal representing a sequencing reaction byproduct proximate thereto, and wherein each of the template nucleic acids is hybridized to a sequencing primer and is bound to a polymerase; (b) introducing a known nucleotide triphosphate into the reaction chambers; (c) detecting incorporation at a 3' end of the sequencing primer of one or more nucleotide triphosphates by a sequencing reaction byproduct if such one or more nucleotide triphosphates are complementary to corresponding nucleotides in the template nucleic acid; (d) washing unincorporated nucleotide triphosphates from the reaction chambers; and (e) repeating steps (b) through (d) until the plurality of template nucleic acids are sequenced. For embodiments where hydrogen ion is measured as a reaction byproduct, the reactions further should be conducted under weak buffer conditions, so that the maximum number of hydrogen ions reacts with a sensor and not extraneous components (e.g. microwell or solid supports that may have surface buffering capacity) or chemical constituents (in particular pH buffering compounds). In one embodiment, a weak buffer allows detection of a pH change of at least ±0.1 in said reaction chamber, or at least ±0.01 in said reaction chambers.

Example 1

Making Polyacrylamide Nucleic Acid Polymer Particles by Membrane Emulsification

This example describes the method and apparatus for production of uniformly sized droplets of aqueous solution in non-miscible continuous phase by extrusion through a micro fabricated plate with multiple through holes (nozzles, orifices) and the subsequent transformation of the emulsion into polymer particles by radical polymerization. The fabrication of the plate with multiple through holes is described in the above references.

A solution of specific amounts of acrylamide and methylene-N,N-bisacrylamide containing a specified concentration of acrodyte 5'-labeled oligonucleotides (primers for PCR) is degassed by bubbling an inert atmosphere (Argon, Nitrogen, Helium) through the solution for a minimum of 30 minutes. Just prior to emulsification, a radical initiator is added. The radical initiator can be a combination of ammonium persulfate (APS) and N, N, N', N'-tetramethylethylenediamine (TMED) which catalyses the radical initiation by APS. The amount of TMED used needs to be carefully adjusted to allow sufficient time for emulsification. APS and V-50 (see below) initiate thermally above ~65 degrees celsius. Alternatively a photoinitiator such 2,2'-Azobis(2-methylpropionamidine)dihydrochloride (V-50) may be used in conjunction with a UV light source with strong emission peaks at 220 nm and 365 nm. The aqueous solution above may be dispersed into a continuous phase via several techniques. For example: The aqueous solution may be subdivided into droplets by a vibrating membrane with several appropriately sized holes (typically 50-70% smaller than the intended diameter of the droplet) after which the droplets are allowed to enter an immiscible continuous phase which may or may not contain surfactants. The droplets may be irradiated with UV prior to entering the continuous phase (after leaving the nozzle, in mid air) or after entering the continuous phase. In one implementation the drops are allowed to polymerize prior to entering the continuous phase which may be miscible with the un-polymerized dispersed phase. In either case, the humidity of the atmosphere needs to be controlled to prevent uncontrolled evaporative shrinking of the droplets and the atmosphere needs to be largely oxygen free to allow radical polymerization in the droplets. An alternative emulsification technique can be described as follows: The aqueous phase is pumped through a porous membrane (with uniformly sized pores) into an immiscible continuous phase. After polymerization, the beads are recovered from the continuous phase by either breaking the emulsion (by addition of n-butanol, n-propanol i-propanol or other appropriate chemicals) followed by centrifugation to pellet the beads in the bottom of the eppendorf tube or filtration through an appropriately sized filter. After washing with an appropriate buffer, the beads can be used for PCR amplification of DNA library elements or direct hybridization of DNA fragments with the reverse complement to the attached oligonucleotide.

Example 2

Making Polyacrylamide Nucleic Acid Polymer Particles by Membrane Emulsification with Batch Mode Initiation This example describes membrane emulsification and the subsequent transformation of the aqueous micelles of the emulsion into polyacrylamide particles by radical polymerization in batch mode using an initiator-saturated oil phase. The steps of the process comprise (a) formation of a gel reaction mixture-in-oil emulsion using a membrane, (b) particle polymerization, and (c) particle extraction and washing.

The following reagents are employed in the process: (a) SNAPP Oil comprises the following mixture: Tegosoft™ DEC oil (730 mL), ABIL WE09 (70 gm), and mineral oil (200 mL) (SNAPP oil is stored under argon); (b) SNAPP Buffer: 1× TE, 0.1% Triton X-100, 0.02% sodium azide; (c) Acrylamide Solution: 50 mg N,N-methylene bisacrylamide, 450 mg acrylamide, 550 uL double distilled $H_2O$ kept under argon; (d) DNA Mix: 10 umol 30-mer acrydite oligonucleotide with 18C spacer in 2.5 mL $H_2O$. Gel Reaction Mixture is formed by mixing the following together under argon for a total volume of 1400 uL: 526.4 uL DNA Mix, 14 mL TMED, 299.6 mL $H_2O$, and 560 mL Acrylamide Solution. Under argon, 1 mL of the Gel Reaction Mixture is added to the upper compartment of a two-compartment rig (see FIGS. 2A & 2B) having an emulsification membrane dividing the upper compartment from the lower compartment, so that the Gel Reaction Mixture flows under gravity from the upper compartment through the emulsification membrane (thereby forming droplets or micelles) into a flow of SNAPP Oil in the lower compartment. SNAPP Oil is driven into the lower chamber at a rate of 2.4 mL/hr. About 50 mL of the SNAPP Oil-Gel Reaction Mixture emulsion is collected in a centrifuge tube, after which it is centrifuged so that the Gel Reaction Mixture micelles are driven to the bottom. All but about 1 mL of the supernatant SNAPP Oil is removed, after which the micelles are resuspended by adding 20 mL of initiator (1,1'-azobis(cyclohexanecarbonitrile))-saturated SNAPP Oil. (Initiator-saturated SNAPP Oil is made by mixing 500 mg initiator in 25 mL SNAPP Oil under argon with vigorous mixing). The resuspended micelles undergo polymerization by placing them in an oven at 90° C. under argon and constant rotation for 2 hr. and 2 min, after which they are removed and immediately place in a 4° C. refrigerator for at least 1 hr. The SNAPP Oil is removed from the polymerized particles by centrifuging to form a pellet followed by resuspension in butanol with vortexing, and then repeating, after which the polymerized particles are resuspended in 0.1% SDS and sonicated for 3 min. The polymerized particles are then twice centrifuged, resuspended in SNAPP Buffer, and sonicated for 3 min, after which they are resuspended in SNAPP Buffer and stored at 4° C.

The size distribution of the above nucleic acid polymer particles may be measured using a Guava flow cytometer after hybridizing a labeled oligonucleotide with a sequence complementary to at least one of those of the nucleic acid polymer particle. An exemplary protocol is as follows: (1) suspend about 5 million particles in 9 µL 1×PBS 0.2% Tween, (2) add 2 µL of 100 µM biotinylated oligonucleotide complement, (3) anneal at 95° C. for 2 min followed by 37° C. for 2 min, (4) centrifuge to remove supernatant, (5) wash 2× with 1× PBS 0.2% Tween, (6) resuspend in 10 µL 1×PBS 0.2% Tween, (7) add 0.5 µL streptavidin-FITC (commercial reagent, e.g. Anaspec, Fremont, Calif.), (8) wash 2× with 1×PBS 0.05 Tween, (9) add to 1 mL 1×PBS 0.05% Tween, and (10) run sample on flow cytometer (e.g. EasyCyte mini, Guava Technologies).

Size distributions of nucleic acid polymer particles may also be measured by staining and counting them using a fluorescent microscope with automatic particle counting software. A series of dilutions of nucleic acid polymer particles are stained with a series of concentrations of a nucleic acid stain, such as SYBR Gold (Invitrogen), after which they are place in separate wells of multi-welled poly-I-lysine coated slides (e.g. Tekdon Inc.). A comparison of particle sizing and counting data from flow system and microscope measurements shows good correlation. CVs of size distributions of samples from a batch of nucleic acid polymer particles, designated B4, was determined by slide counting (described above) and by flow cytometry counting (described above). For slide counting, three samples of particles (4.32 million/uL) were analyzed and coefficients of variation were determined to be 12.9%, 13.8%, and 9.6%, respectively. A single sample of particles (3.8 million/uL) was analyzed and a coefficient of variation was determined to be 5.88%.

While the present invention has been described with reference to several particular example embodiments, those skilled in the art will recognize that many changes may be made thereto without departing from the spirit and scope of the present invention. The present invention is applicable to a variety of implementations and other subject matter, in addition to those discussed above.

Definitions

Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999).

"Amplicon" means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences that contain a common region that is amplified, for example, a specific exon sequence present in a mixture of DNA fragments extracted from a sample.

Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800, 159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. As used herein, the term "amplifying" means performing an amplification reaction. An "reaction mixture," including an "amplification reaction mixture," means a solution containing all the necessary reactants for performing a reaction, which may include, but not be limited to, buffering agents to maintain pH at a selected level during a reaction, salts, co-factors, scavengers, and the like. A "solid phase amplicon" means a solid phase support, such as a particle or bead, having attached a clonal population of nucleic acid sequences, which may have been produced by a process such as emulsion PCR, or like technique. One aspect of the invention is solid phase amplicons comprising nucleic acid polymer particles. In some embodiments, amplicons may be produced by isothermal reactions, such as rolling circle amplification reactions, NASBAs, or helicase-mediated amplification reactions, e.g. U.S. Pat. No. 7,282, 328, which is incorporated by reference.

"Microwell," which is used interchangeably with "reaction chamber," means a special case of a "reaction confinement region," that is, a physical or chemical attribute of a solid substrate that permit the localization of a reaction of interest. Reaction confinement regions may be a discrete region of a surface of a substrate that specifically binds an analyte of interest, such as a discrete region with oligonucleotides or antibodies covalently linked to such surface. Usually reaction confinement regions are hollows or wells having well-defined shapes and volumes which are manufactured into a substrate. These latter types of reaction confinement regions are referred to herein as microwells or reaction chambers, and may be fabricated using conventional microfabrication techniques, e.g. as disclosed in the following references: Doering and Nishi, Editors, Handbook of Semiconductor Manufacturing Technology, Second Edition (CRC Press, 2007); Saliterman, Fundamentals of BioMEMS and Medical Microdevices (SPIE Publications, 2006); Elwenspoek et al, Silicon Micromachining (Cambridge University Press, 2004); and the like. Preferable configurations (e.g. spacing, shape and volumes) of microwells or reaction chambers are disclosed in Rothberg et al, U.S. patent publication 2009/0127589; Rothberg et al, U.K. patent application GB24611127, which are incorporated by reference. Microwells may have square, rectangular, or octagonal cross sections and be arranged as a rectilinear array on a surface. Microwells may also have hexagonal cross sections and be arranged as a hexagonal array, which permit a higher density of microwells per unit area in comparison to rectilinear arrays. Exemplary configurations of microwells are as follows: In some embodiments, the reaction chamber array comprises $10^2$, $10^3$, $10^4$, $10^5$, $10^6$ or $10^7$ reaction chambers. As used herein, an array is a planar arrangement of elements such as sensors or wells. The array may be one or two dimensional. A one dimensional array is an array having one column (or row) of elements in the first dimension and a plurality of columns (or rows) in the second dimension. The number of columns (or rows) in the first and second dimensions may or may not be the same. Preferably, the array comprises at least 100,000 chambers. Preferably, each reaction chamber has a horizontal width and a vertical depth that has an aspect ratio of about 1:1 or less. Preferably, the pitch between the reaction chambers is no more than about 10 microns. Briefly, in one embodiment microwell arrays may be fabricated as follows: After the semiconductor structures of a sensor array are formed, the microwell structure is applied to such structure on the semiconductor die. That is, the microwell structure can be formed right on the die or it may be formed separately and then mounted onto the die, either approach being acceptable. To form the microwell structure on the die, various processes may be used. For example, the entire die may be spin-coated with, for example, a negative photoresist such as Microchem's SU-8 2015 or a positive resist/polyimide such as HD Microsystems HD8820, to the desired height of the microwells. The desired height of the wells (e.g., about 3-12 µm in the example of one pixel per well, though not so limited as a general matter) in the photoresist layer(s) can be achieved by spinning the appropriate resist at predetermined rates (which can be found by reference to the literature and manufacturer specifications, or empirically), in one or more layers. (Well height typically may be selected in correspondence with the lateral dimension of the sensor pixel, preferably for a nominal 1:1-1.5:1 aspect ratio, height:width or diameter.) Alternatively, multiple layers of different photoresists may be applied or another form of dielectric material may be deposited. Various types of chemical vapor deposition may also be used to build up a layer of materials suitable for microwell formation therein. In one embodiment, microwells are formed in a layer of tetra-methyl-ortho-silicate (TEOS). The invention encompasses an apparatus comprising at least one two-dimensional array of reaction chambers, wherein each reaction chamber is coupled to a chemically-sensitive field effect transistor ("chemFET") and each reaction chamber is no greater than 10 µm$^3$ (i.e., 1 pL) in volume. Preferably, each reaction chamber is no greater than 0.34 pL, and more preferably no greater than 0.096 pL or even 0.012 pL in volume. A reaction chamber can optionally be $2^2$, $3^2$, $4^2$, $5^2$, $6^2$, $7^2$, $8^2$, $9^2$, or $10^2$ square microns in cross-sectional area at the top. Preferably, the array has at least $10^2$, $10^3$, $10^4$, $10^5$, $10^6$, $10^7$, $10^8$, $10^9$, or more reaction chambers. The reaction chambers may be capacitively coupled to the chemFETs, and preferably are capacitively coupled to the chemFETs.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates.

Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, concatemeric PCR, and the like. Reaction volumes range from a few hundred nanoliters, e.g. 200 nL, to a few hundred μL, e.g. 200 μL.

"Polymer network" means a structure comprising covalently connected subunits (monomers, crosslinkers, and the like) in which all such subunits are connected to every other subunit by many paths through the polymer phase, and wherein there are enough polymer chains bonded together (either physically or chemically) such that at least one large molecule is coextensive with the polymer phase (i.e. the structure is above its gel point). Preferably a polymer network has a volume in the range of from 65 aL to 15 pL, or from 1 fL to 1 pL.

"Polynucleotide" or "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moities, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, $2^{nd}$ Edition (Cold Spring Harbor Press, New York, 2003).

"Sample" in one aspect means a quantity of material from a biological, environmental, medical, or patient source in which detection or measurement of one or more analytes is sought. A sample may also include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, needle aspirates, and the like. Biological samples also may be obtained from animals. Environmental samples include environmental material such as surface matter, soil, water and industrial samples, as well as samples obtained from food and dairy processing instruments, apparatus, equipment, utensils, and the like. In another aspect, "sample" means a material or substance extracted, partially purified, separated, or otherwise obtained by sample preparation techniques from a sample as defined in the previous sentences (collectively referred to as "extracted material"). Such extracted materials that are occasionally referred to herein as "samples" include but are not limited to nucleic acids (for example, DNA or RNA extracted material), protein extracted material, lipid extracted material, and the like.

What is claimed is:

1. A method for forming a particle, the method comprising:

suspending an emulsion in an initiator-saturated oil-based continuous phase, the emulsion comprising the continuous phase and a disperse phase, the disperse phase including an acrylamide monomer, a bis-acrylamide crosslinker, a surfactant, and an acrydite oligonucleotide in an aqueous solution;

heating the emulsion to polymerize the acrylamide monomer, bis-acrylamide crosslinker and acrydite oligonucleotide to form acrylamide gel particles having a plurality of oligonucleotides attached through a polymer network of the acrylamide gel; and removing the initiator-saturated oil-based continuous phase; and resuspending the acrylamide gel particles in a buffered aqueous solution, wherein the acylamide gel particles have a coefficient of variance of volume of not greater than 15%, a total monomer percentage of the acrylamide gel particles is in a range of 3% to 20%, and the acrylamide gel particles are permeable to proteins having a size in the range of 50 kilodaltons to 200 kilodaltons.

2. The method of claim 1, further comprising cooling the emulsion following polymerization and prior to removing the continuous phase.

3. The method of claim 1, wherein removing the continuous phase includes centrifuging to form a pellet of the acrylamide gel particles.

4. The method of claim 1, further comprising resuspending in butanol, centrifuging, and removing the butanol, following removing the initiator-saturated oil-based continuous phase and prior to resuspending the acrylamide gel particles in the buffered aqueous solution.

5. The method of claim 1, wherein the acrylamide gel particles include the oligonucleotide through their volume at an average density of at least $6.9 \times 10^4$ per $\mu m^3$.

6. The method of claim 1, further comprising forming the emulsion with an oil-based continuous phase and the disperse phase, and removing the oil-based continuous phase.

7. The method of claim 6, wherein removing the oil-based continuous phase includes centrifuging the emulsion.

8. The method of claim 6, wherein forming the emulsion includes extruding the disperse phase through a membrane into the oil-based continuous phase.

9. The method of claim 8, wherein the membrane has orifices having a diameter of 25% to 35% of the diameter of the acrylamide gel particles.

10. The method of claim 1, wherein heating includes heating in a heated tube.

11. The method of claim 1, wherein heating includes heating in an oven.

12. The method of claim 1, wherein the acrylamide gel particles have an average diameter of from about 0.5 $\mu m$ to about 10 $\mu m$.

13. The method of claim 1, wherein the total monomer percentage of the acrylamide gel particles is in a range of 5% to 10%.

14. The method of claim 1, wherein the acrylamide gel particles have an average pore size in a range of 20 nm to 150 nm.

15. The method of claim 1, further comprising:

combining a library of polynucleotides and the acrylamide gel particles in an amplification reaction mixture, wherein at least one polynucleotide includes a primer binding site complementary to the oligonucleotide; and performing an amplification reaction in the amplification reaction mixture, thereby forming an amplicon library including a plurality of particles having a clonal population of polynucleotides from the acrylamide gel particles.

16. The method of claim 15, wherein the amplification reaction is a polymerase chain reaction.

17. The method of claim 15, wherein the amplification reaction is an isothermal reaction.

18. The method of claim 15, introducing at least one acrylamide gel particle having a clonal population of polynucleotides into a reaction chamber coupled to a field effect transistor.

19. The method of claim 18, wherein the field effect transistor is an ion-sensitive field effect transistor.

20. The method of claim 1, wherein the acrylamide gel particles are substantially spherical or spheroidal in shape.

* * * * *